(12) United States Patent
Whitehead et al.

(10) Patent No.: US 8,162,874 B2
(45) Date of Patent: Apr. 24, 2012

(54) MEDICAL PUMP WITH FIXED STROKE LENGTH

(75) Inventors: Nicholas R. Whitehead, Hopkins, MN (US); John Michael Gray, Brooklyn Park, MN (US); James M. Haase, Maplewood, MN (US); Cynthia R. Nelson Konen, Anoka, MN (US); Thomas W. Hovind, Andover, MN (US); Dale A. Young, Lake Elmo, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/755,888

(22) Filed: Apr. 7, 2010

(65) Prior Publication Data

US 2010/0280447 A1    Nov. 4, 2010

Related U.S. Application Data

(60) Provisional application No. 61/174,401, filed on Apr. 30, 2009.

(51) Int. Cl.
*A61M 31/00* (2006.01)
(52) U.S. Cl. ........................................................ 604/67
(58) Field of Classification Search ................... 604/67, 604/151, 890.1, 891.1
See application file for complete search history.

(56) References Cited

U.S. PATENT DOCUMENTS

| | | | |
|---|---|---|---|
| 4,692,147 A | 9/1987 | Duggan | |
| 6,422,057 B1 | 7/2002 | Anderson | |
| 6,572,583 B1 | 6/2003 | Olsen et al. | |
| 6,635,048 B1 | 10/2003 | Ullestad et al. | |
| 6,769,462 B2 * | 8/2004 | Larson et al. | 141/83 |
| 2003/0040780 A1 | 2/2003 | Haeg et al. | |
| 2003/0055406 A1 | 3/2003 | Lebel et al. | |
| 2003/0192616 A1 * | 10/2003 | Larson et al. | 141/2 |
| 2005/0240167 A1 | 10/2005 | Gray et al. | |
| 2006/0009921 A1 * | 1/2006 | Shelton et al. | 702/31 |
| 2006/0095020 A1 | 5/2006 | Casas et al. | |
| 2006/0206067 A1 | 9/2006 | Ferek-Petric | |
| 2006/0206099 A1 | 9/2006 | Olsen | |
| 2008/0097287 A1 | 4/2008 | Nelson et al. | |

(Continued)

FOREIGN PATENT DOCUMENTS

WO    WO 03/022326 A2    3/2003

(Continued)

OTHER PUBLICATIONS

Notification of Transmittal of the International Search Report and the Written Opinion of the International Searching Authority, for patent application No. PCT/US2010/030709, mailed Nov. 18, 2010, 10 pages.

(Continued)

*Primary Examiner* — Nicholas Lucchesi
*Assistant Examiner* — Aarti B Berdichevsky
(74) *Attorney, Agent, or Firm* — Shumaker & Sieffert, P.A.

(57) ABSTRACT

A method comprises measuring a volume of fluid delivered per pump stroke for each of a plurality of substantially identical medical pumps. The substantially identical medical pumps each have a fixed stroke length. The method further comprises: storing indications of the measured volumes on one or more data storage mediums; and for each of the plurality of substantially identical medical pumps, generating a separate therapy control program based on the indication of the measured volume associated with that one of the plurality of substantially identical medical pumps.

13 Claims, 14 Drawing Sheets

U.S. PATENT DOCUMENTS

| | | | |
|---|---|---|---|
| 2008/0286132 A1 | 11/2008 | Haase et al. | |
| 2008/0312595 A1* | 12/2008 | Elmouelhi et al. | 604/151 |
| 2009/0270805 A1 | 10/2009 | Das | |
| 2010/0280348 A1* | 11/2010 | Wenzel et al. | 600/365 |
| 2010/0280501 A1* | 11/2010 | Young et al. | 604/891.1 |
| 2010/0280502 A1* | 11/2010 | Hovind et al. | 604/891.1 |
| 2011/0060531 A1* | 3/2011 | Sugo et al. | 702/19 |
| 2011/0166522 A1* | 7/2011 | Haase et al. | 604/151 |

FOREIGN PATENT DOCUMENTS

| | | |
|---|---|---|
| WO | WO 03/023226 A1 | 3/2003 |
| WO | WO 2008/154090 A1 | 12/2008 |

OTHER PUBLICATIONS

U.S. Appl. No. 12/755,872, by Dale A. Young et al., filed Apr. 7, 2010.

U.S. Appl. No. 12/755,916, by Nicholas R. Whitehead et al., filed Apr. 7, 2010.

U.S. Appl. No. 61/174,457, by Dale A. Young et al., filed Apr. 30, 2009.

U.S. Appl. No. 61/174,401, by Nicholas R. Whitehead et al., filed Apr. 30, 2009.

* cited by examiner

MEDICAL PUMP WITH FIXED STROKE LENGTH

This application claims the benefit of U.S. Provisional Application No. 61/174,401, filed Apr. 30, 2009, the entire content of which is incorporated by reference herein.

TECHNICAL FIELD

The disclosure relates to medical pumps, and more particularly, but without limitation, to implantable medical devices including medical pumps.

BACKGROUND

Medical pumps can be used to treat a variety of physiological, psychological, and emotional conditions. For some medical conditions, medical pumps can restore an individual to a more healthful condition and a fuller life. For example, medical pumps may be used for chronic delivery of therapeutic agents, such as drugs. As one specific example, a medical pump may be used to deliver insulin to a diabetic patient. Other examples include delivery of pain relief medication, e.g., to the intrathecal or epidural space of a patient, to alleviate chronic pain.

Some medical pumps are implantable. Implantable medical pumps may be implanted at a location in the body of a patient and deliver a fluid medication through a catheter to a selected delivery site within the body of a patient. Typically, a catheter connects to an outlet of a medical pump outlet and delivers a therapeutic agent at a programmed infusion rate to a predetermined location to treat a medical condition. An implantable medical pump is implanted by a clinician into a patient at a location that interferes as little as practicable with patient activity. For example, implantable medical pumps are often implanted subcutaneously in the lower abdomen of a patient. Implantable medical pumps may include self-sealing fluid reservoirs accessible through ports to facilitate in-service refilling by percutaneous injection.

SUMMARY

In general, the disclosure relates to medical pumps having a fixed stroke length. The disclosure also relates to techniques for calibrating therapy control programs for individual medical pumps based on a measured volume of fluid delivered per pump stroke to account for variability of the volume of fluid delivered per pump stroke among a plurality of substantially identical pumps.

In one example, the disclosure is directed to a method comprising: measuring a volume of fluid delivered per pump stroke for each of a plurality of substantially identical medical pumps. The substantially identical medical pumps each have a fixed stroke length. The method further comprises: storing indications of the measured volumes on one or more data storage mediums; and for each of the plurality of substantially identical medical pumps, generating a separate therapy control program based on the indication of the measured volume associated with that one of the plurality of substantially identical medical pumps.

In another example, the disclosure is directed to a computer-readable data-storage medium comprising instructions that cause a programmable processor to: access an indication of a volume of fluid delivered per pump stroke of a medical pump; and control the medical pump to deliver a specified quantity of therapeutic fluid to a target site within a patient based on the indication.

In another example, the disclosure is directed to a medical pump assembly comprising: a magnetic cup forming a recess. The magnetic cup includes a protrusion within the recess, and the cup forms a central aperture through the protrusion. The medical pump assembly further comprises: a one-way valve that controls fluid flow within the central aperture; an electromagnetic coil within the recess and circumscribing the protrusion; a piston within the central aperture; a magnetic pole attached to the piston; and a cover enclosing the magnetic pole between an interior surface of the cover and the electromagnetic coil. The cover includes one or more fixed protrusions on the interior surface of the cover, and wherein the protrusions set a stroke length of the piston.

In another example, the disclosure is directed to a system comprising: a medical pump with a fixed stroke length; and a means for delivering a specified quantity of therapeutic fluid to a patient with the medical pump according to an indication of a volume of fluid delivered per pump stroke of the medical pump.

In another example, the disclosure is directed to a system comprising: a medical pump with a fixed stroke length; a memory storing an indication of a volume of fluid delivered per pump stroke of the medical pump; a programmer including a user interface to receive an indication of a specified quantity of fluid to be transferred by the pump from a user; and a processor that generates a therapy control program for operating the medical pump based on the indication stored in the memory and the indication of the specified quantity of fluid.

The details of one or more examples are set forth in the accompanying drawings and the description below. Other features, objects, and advantages will be apparent from the description and drawings, and from the claims.

DETAILED DESCRIPTION

Figure 1:
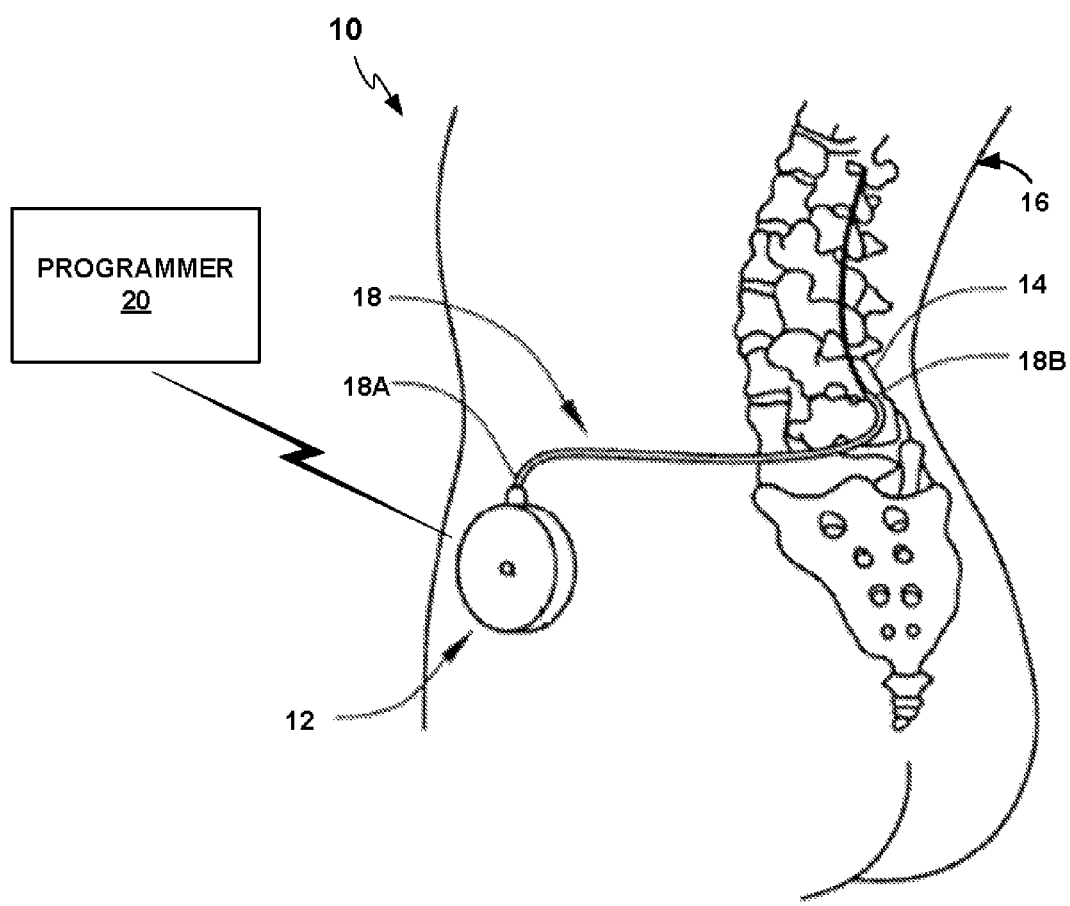
FIG. 1 is a conceptual diagram illustrating an example of a fluid delivery system, which includes an implantable medical device (IMD) with a medical pump that is configured to deliver a therapeutic agent to a patient via a catheter.

Medical devices are useful for treating, managing or otherwise controlling various patient conditions or disorders, such as, but not limited to, pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices may be configured to deliver one or more therapeutic agents, alone or in combination with other therapies, such as electrical stimulation, to one or more target sites within a patient. For example, in some cases, a medical pump may deliver one or more pain-relieving drugs to patients with chronic pain, insulin to a patient with diabetes, or other fluids to patients with different disorders. A medical pump may be implanted in the patient for chronic therapy delivery (e.g., longer than a temporary, trial basis) or temporary delivery. Example therapeutic agents deliverable with medical pumps as described herein include, but are not limited to, insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

A medical pump may be configured to deliver a therapeutic agent from the fluid reservoir to a patient according to a therapy program, which may, for example, specify a delivery rate of a fluid delivered to the patient by the medical pump. As another example, a therapy program may adjust the delivery rate automatically based on physiological characteristics of a patient. In some instances, an external controller may be used to alter the therapy program as well as send and receive data relating to the operation of the medical pump. In different examples, an external controller may be operated by either one or both of a clinician and the patient.

Drug therapies may dictate a specific target dose resolution in order meet therapy efficacy requirements; insulin therapy is one example. In accordance with the techniques disclosed herein, fully functional pump subassemblies can be built, calibrated and labeled. The calibration may include precisely measuring the fluid volume for a single pump stoke and storing a representation of that volume in memory for future therapy delivery. In addition, the techniques described herein provide for pump subassemblies with customized dosage resolutions, i.e., stroke volume and drug types (e.g. insulin) that can be "dropped in" (like a car engine) to a common pump framework, such as a bulkhead.

In addition, in accordance with the techniques disclosed herein, fully functional pump subassemblies may greatly reduce development cycle time, manufacturing cost, scrap, and piece part costs since the pump subassemblies can be built on a feeder line and functionally tested as standalone components prior to being integrated into the pump framework. Further aspects of this disclosure include pump subassemblies designs with welding features that provide high weld yields, i.e., a low rate of defective welds.

In accordance with the techniques disclosed herein, a fully functional pump subassembly can include an electromagnetic drive coil, electromagnetic material to drive flux, a reciprocating electromagnetic actuator, a piston, a bore, a check valve, a stroke length setter, and a bacterial filter. In some examples, a fully functional pump subassembly includes a titanium sleeve which comprises the pump bore, spring recess, valve seat and valve fastening features integrated with electromagnetic drive coil components. A titanium weld ring is integrated to electromagnetic drive coil components to facilitate hermetically attaching pump components. A fully functional pump subassembly may include a bacterial filter with a cover including stroke setting features. Stroke setting feature integrated to cover that encloses the pumping actuator can provide a hermetic flow path of subassembly. In addition, a fully functional pump subassembly can include a valve assembly housed within the titanium sleeve. A "sandwich weld" can be used to permanently and hermetically weld the electromagnetic drive coil components to the pump enclosure component by sealing the titanium weld ring, a barrier plate over the drive coil and the cover with a single weld. Some examples included in this disclosure can provide for testing pumping functionality (seal testing, electrical testing and mechanical pump operation testing) of the pump subassembly as a standalone component, i.e., without installing the pump subassembly within the common pump framework. As referred to herein, mechanical testing includes testing the mechanical operation of the pump piston and or pump valve and electrical testing includes testing the functionality and/or integrity of the pump coil. Seal testing includes looking for defects or leaks in welds and/or other seals of a pump or pump subassembly. These and other examples are described with respect to the figures included in this disclosure.

FIG. 1 is a conceptual diagram illustrating an example of a therapy system 10 including IMD 12, which is configured to deliver at least one therapeutic agent, such as a pharmaceutical agent, insulin, pain relieving agent, anti-inflammatory agent, gene therapy agent, or the like, to a target site within patient 16 via catheter 18, which is coupled to IMD 12. In one example, catheter 18 may comprise a plurality of catheter segments. In other examples, catheter 18 may be a unitary catheter. In the example shown in FIG. 1, the target site is proximate to spinal cord 14 of patient 16. A proximal end 18A of catheter 18 is coupled to IMD 12, while a distal end 18B of catheter 18 is located proximate to the target site. Therapy system 10 also includes external programmer 20, which wirelessly communicates with IMD 12 as needed, such as to provide or retrieve therapy information or control aspects of therapy delivery (e.g., modify the therapy parameters, turn IMD 12 on or off, and so forth). While patient 16 is generally referred to as a human patient, other mammalian or non-mammalian patients are also contemplated.

Generally, IMD 12 has an outer housing that is constructed of a biocompatible material that resists corrosion and degradation from bodily fluids, such as titanium or biologically inert polymers. IMD 12 may be implanted within a subcutaneous pocket close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent.

In accordance with the techniques described herein, IMD 12 includes a modular medical pump. A modular medical pump is a medical pump that facilitates assembly of at least a portion of the pump components separately from the pump housing (or bulkhead) of IMD 12 containing a fluid a fluid reservoir, a port and a medical pump subassembly. An IMD with a modular medical pump may have a lower production cost compared to an IMD in which all or substantially all of the medical pump assembly occurs in conjunction with a bulkhead.

Catheter 18 may be coupled to IMD 12 either directly or with the aid of a catheter extension (not shown in FIG. 1). In the example shown in FIG. 1, catheter 18 traverses from the implant site of IMD 12 to one or more target sites proximate to spine 14. Catheter 18 is positioned such that one or more fluid delivery outlets of catheter 18 are proximate to the one or more target sites within patient 16. IMD 12 delivers a therapeutic agent to the one or more target sites proximate to spinal cord 14 with the aid of catheter 18. IMD 12 can be configured for intrathecal drug delivery into the intrathecal space, as well as epidural delivery into the epidural space, both of which surround spinal cord 14. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord 14. The intrathecal space is within the subarachnoid space of spinal cord 14, which is past the epidural space and dura mater and through the theca of spinal cord 14.

As already mentioned, in some applications, therapy system 10 can be used to reduce pain experienced by patient 16. In such an application, IMD 12 can deliver one or more therapeutic agents to patient 16 according to one or more dosing programs that set forth different therapy parameters, such as a therapy schedule specifying programmed doses, dose rates for the programmed doses, and specific times to deliver the programmed doses. The dosing programs may be a part of a program group for therapy, where the group includes a plurality of dosing programs and/or therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. Patient 16 or a clinician may select and/or generate additional dosing programs for use by IMD 12 via external programmer 20 at any time during therapy or as designated by the clinician.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 16 to view and modify therapy parameters. The clinician programmer may include additional or alternative programming features, relative to the patient programmer. For example, more complex or sensitive tasks may only be allowed by the clinician programmer to prevent patient 16 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate through the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 18, the position of catheter 18 within patient 16, the type and amount, e.g., by volume of therapeutic agent(s) delivered by IMD 12, a refill interval for the therapeutic agent(s), a baseline orientation of at least a portion of IMD 12 relative to a reference point, therapy parameters of therapy programs stored within IMD 12 or within programmer 20, and any other information the clinician desires to program into IMD 12. In accordance with some examples of this disclosure, the refill interval may be based on an expiration time for the therapeutic agent(s).

The clinician uses programmer 20 to program IMD 12 with one or more therapy programs that define the therapy delivered by IMD 12. During a programming session, the clinician may determine one or more dosing programs that may provide effective therapy to patient 16. Patient 16 may provide feedback to the clinician as to the efficacy of a specific program being evaluated or desired modifications to the dosing program. Once the clinician has identified one or more programs that may be beneficial to patient 16, patient 16 may continue the evaluation process and determine which dosing program or therapy schedule best alleviates the condition of patient 16 or otherwise provides efficacious therapy to patient 16.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. IMD 12 may include a feature that prevents dosing the therapeutic agent in a manner inconsistent with the dosing program. Programmer 20 may assist the clinician in the creation/identification of dosing programs by providing a methodical system of identifying potentially beneficial therapy parameters.

A dosage of a therapeutic agent, such as a drug, may be expressed as an amount of drug, e.g., measured in milligrams, provided to the patient over a particular time interval, e.g., per day or twenty-four hour period. This dosage amount may convey to the caregiver an indication of the probable efficacy of the drug and the possibility of side effects of the drug. In general, a sufficient amount of the drug should be administered in order to have a desired therapeutic effect, such as pain relief. However, the amount of the drug administered to the patient should be limited to a maximum amount, such as a maximum daily dose, in order not to avoid potential side effects. Program information specified by a user via programmer 20 may be used to control dosage amount, dosage rate, dosage time, maximum dose for a given time interval (e.g., daily), or other parameters associated with delivery of a drug or other fluid by IMD 12. Dosage may also prescribe particular concentrations of active ingredients in the therapeutic agent delivered by IMD 12 to patient 16.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 16 may be a location proximate to sacral nerves (e.g., the S2, S3, or S4 sacral nerves) in patient 16 or any other suitable nerve, organ, muscle or muscle group in patient 16, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. As further examples, catheter 18 may be positioned to deliver a therapeutic agent to help manage peripheral neuropathy or post-operative pain mitigation, ilioinguinal nerve therapy, intercostal nerve therapy, gastric stimulation for the treatment of gastric motility disorders and/or obesity, muscle stimulation, for mitigation of other peripheral and localized pain (e.g., leg pain or back pain). As another example, catheter 18 may be positioned to deliver a therapeutic agent to a deep brain site or within the heart (e.g., intraventricular delivery of the agent). Delivery of a therapeutic agent within the brain may help manage any number of disorders or diseases. Example disorders may include depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

Examples of therapeutic agents that IMD 12 may be configured to deliver include, but are not limited to, insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics.

Figure 2:
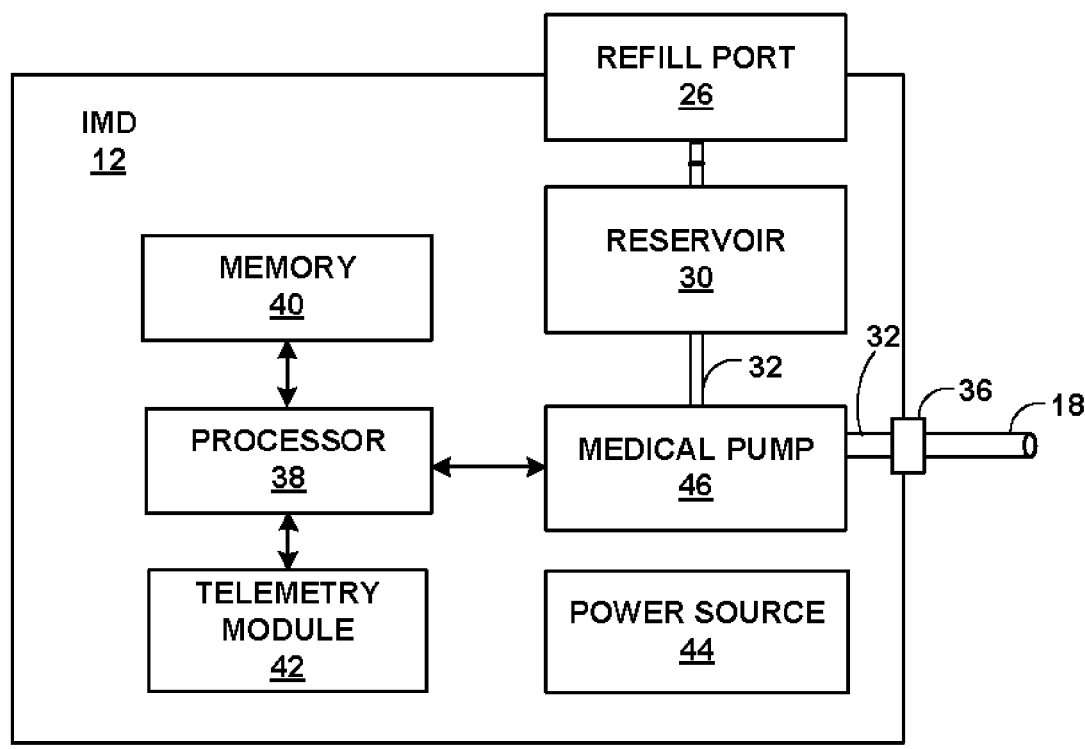
FIG. 2 is functional block diagram illustrating an exemplary IMD with a medical pump.

FIG. 2 is a functional block diagram illustrating components of an example of IMD 12, which includes refill port 26, reservoir 30, processor 38, memory 40, telemetry module 42, power source 44, medical pump 46, internal tubing 32, and catheter connection port 36. As discussed in further detail below, medical pump 46 may facilitate mechanical, electrical and seal testing as a standalone component. Catheter connection port 36 is one example of a port for delivering a therapeutic fluid to a patient; in other examples, IMD 12 may deliver a therapeutic agent without a catheter. Medical pump 46 may be a mechanism that delivers a therapeutic agent in some metered or other desired flow dosage to the therapy site within patient 16 from reservoir 30 via the catheter 18. Refill port 26 may comprise a self-sealing injection port. The self-selaing injection port may include a self-sealing membrane to prevent loss of therapeutic agent delivered to reservoir 30 via refill port 26. After a delivery system, e.g., a hypodermic needle, penetrates the membrane of refill port 26, the membrane may seal shut when the needle is removed from refill port 26. Internal tubing 32 is a segment of tubing that runs from reservoir 30, around or through medical pump 46 to catheter connection port 36.

Processor 38 controls the operation of medical pump 46 with the aid of instructions associated with program information that is stored in memory 40. For example, the instructions may define dosing programs that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of the dosage rate at which the fluid is delivered. In other examples, a quantity of the agent may be delivered according to one or more physiological characteristics of a patient, e.g., physiological characteristics sensed by one or more sensors (not shown) implanted within a patient as part of therapy system 10 (FIG. 1). Components described as processors within IMD 12 and external programmer 20 may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 40 may include any volatile or non-volatile media, such as a random access memory (RAM), read only memory (ROM), non-volatile RAM (NVRAM), electrically erasable programmable ROM (EEPROM), flash memory, and the like. As mentioned above, memory 40 may store program information including instructions for execution by processor 38, such as, but not limited to, therapy programs, historical therapy programs, timing programs for delivery of fluid from reservoir 30 to catheter 18, and any other information regarding therapy of patient 16. Memory 40 may include separate memories for storing instructions, patient information, therapy parameters (e.g., grouped into sets referred to as "dosing programs"), therapy adjustment information, program histories, and other categories of information such as any other data that may benefit from separate physical memory modules.

Telemetry module 42 in IMD 12, as well as telemetry modules in a controller, such as programmer 20, may accomplish communication by RF communication techniques. In addition, telemetry module 42 may communicate with programmer 20 via proximal inductive interaction of IMD 12 with external programmer 20. Processor 38 controls telemetry module 42 to send and receive information.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

FIGS. 3-6 illustrate components of medical pump 100. For example, medical pump 100 may be part of an IMD, such as IMD 12 (FIG. 1). Medical pump 100 includes modular pump coil subassembly 120, piston/pole subassembly 160, cover 170, bulkhead 180 and filter 190. In accordance with the techniques described herein, the configuration of medical pump 100 facilitates electrical and seal integrity testing of modular pump coil subassembly 120 as a standalone component, i.e., prior to assembly of modular pump coil subassembly 120 within bulkhead 180.

Figure 3:
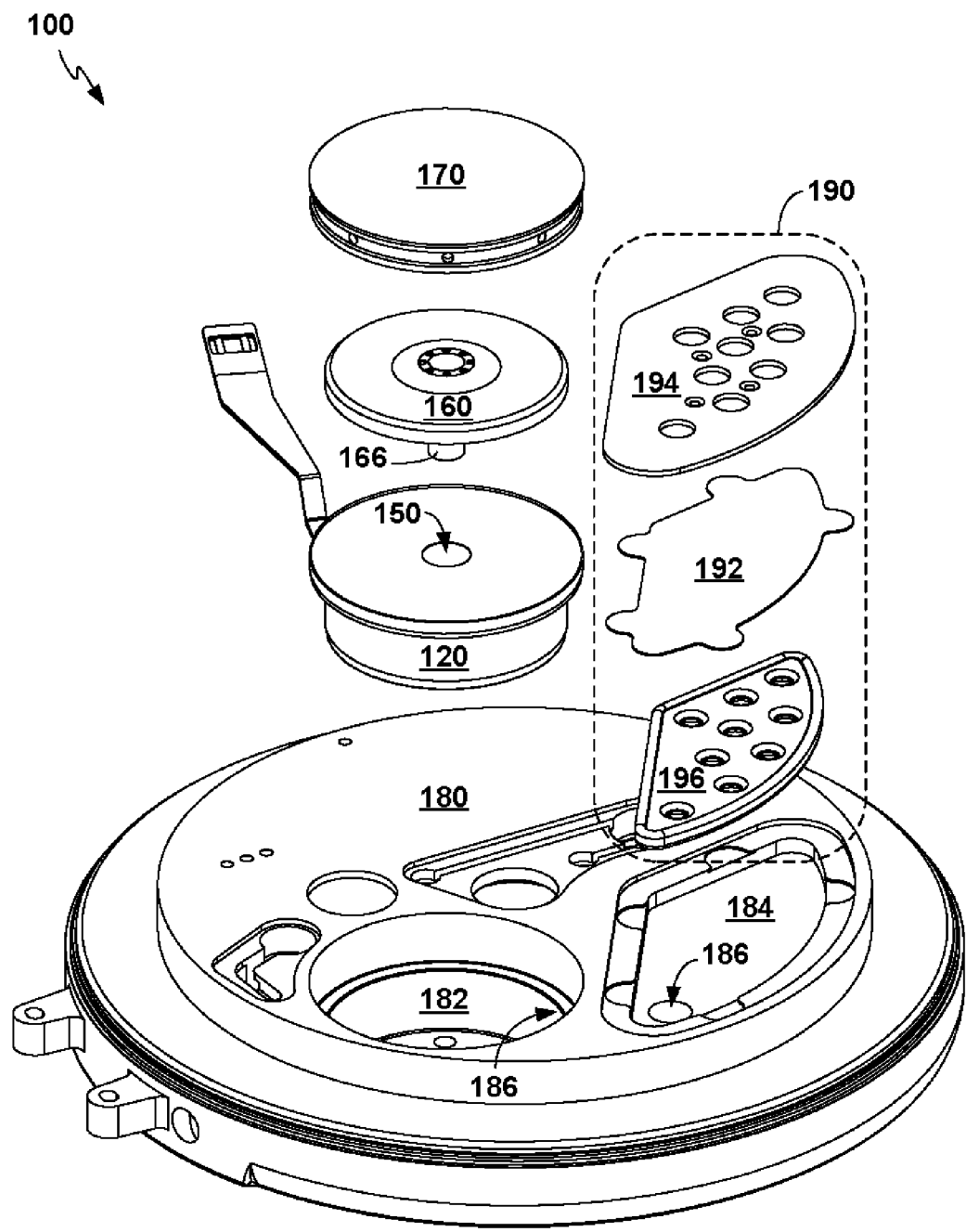
FIGS. 3-6 illustrate components of an exemplary modular medical pump that facilitates seal testing of a pump coil subassembly.

As shown in FIG. 3, bulkhead 180 includes cup-mounting bay 182 to receive modular pump coil subassembly 120 and filter-mounting bay 184 to receive filter 190. Fluid passageway 186 connects cup-mounting bay 182 to filter-mounting bay 184. Bulkhead 180 comprises a biocompatible material. As examples, bulkhead 180 may include a stainless steel alloy, a titanium alloy or other biocompatible material.

Figure 4A:
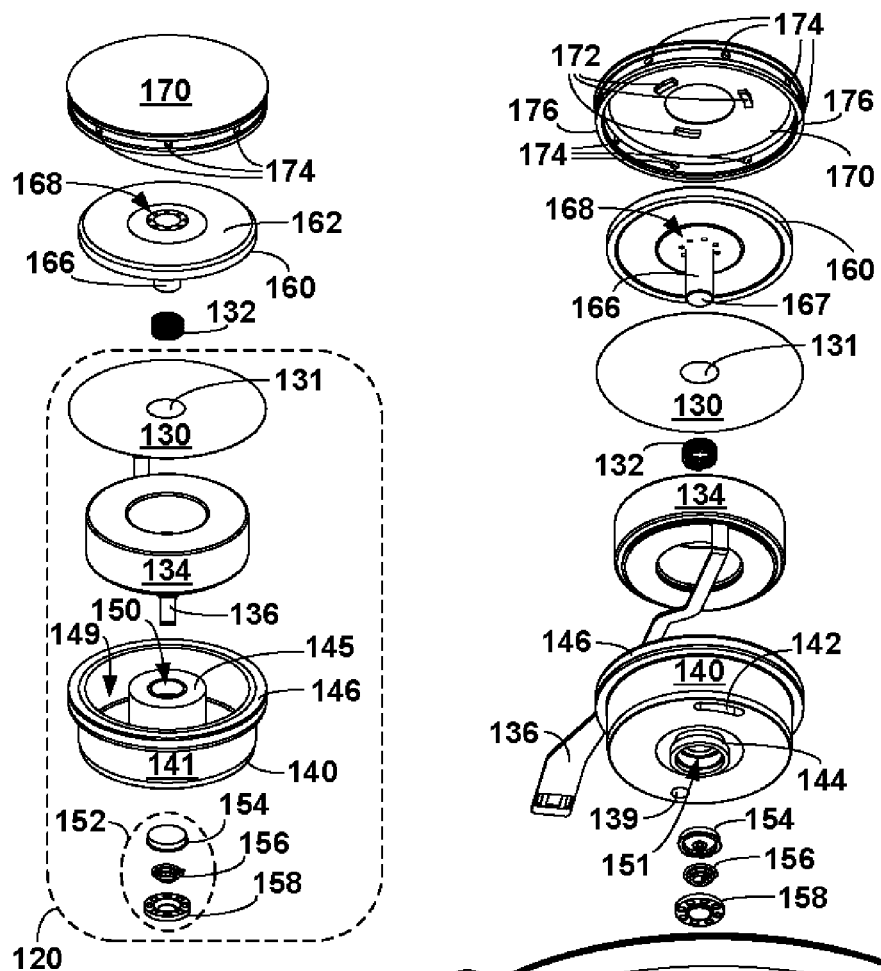

During the operation of medical pump 100, therapeutic fluid flows through filter 190 and into cup-mounting bay 182 via fluid passageway 186. Within cup-mounting bay 182, the fluid enters an enclosure including piston/pole subassembly 160 through holes 174 in cover 170. Once within the enclosure under cover 170, the fluid enters central aperture 150 and is pushed by the motion of piston 166 through one-way valve 152 (FIG. 4A). After passing through valve 152, the therapeutic fluid is directed to one or more target sites within a patient. For example, as shown in FIG. 1, a catheter may be used to direct therapeutic fluid from a medical pump to a target site within a patient.

Filter 190 includes three elements: filter cover 194, filter element 192 and filter base 196. Base 196 forms a seal with filter-mounting bay 184 to prevent any therapeutic fluid from bypassing filter element 192 prior to entering fluid passageway 186. Filter cover 194 serves to compress filter element 192 and base 196 to provide a seal between filter element 192 and base 196 as well as a seal between base 196 and bulkhead 180. Filter cover 194 may be attached to bulkhead 180 by interference fit, screws (not shown) or other suitable techniques. Each of the elements of filter 190 comprise corrosion-resistant materials. As an example, base 196 may comprise a deformable material, such as a polymer or silicone rubber. In other examples, base 196 may comprise a stainless steel or other suitable material. As another example, cover 194 may comprise a polymer, a stainless steel or other suitable material.

Figure 4B:
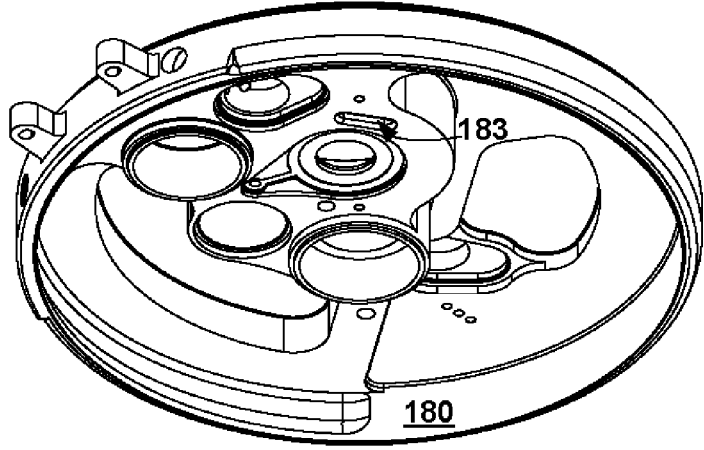

Pump coil subassembly 120 operates to drive piston/pole subassembly 160 during a pump stroke of medical pump 100. The components of modular pump coil subassembly 120 are shown in FIGS. 4A-4B. Pump coil subassembly 120 includes cup assembly 140, electromagnetic coil 134, barrier plate 130 and one-way valve 152. Electromagnetic coil 134 fits underneath barrier plate 130 and within recess 149 of cup assembly 140. In addition, one-way valve 152 seals against seat 151 within the end of sleeve 144 of cup assembly 140 opposite barrier plate 130.

Figure 5:
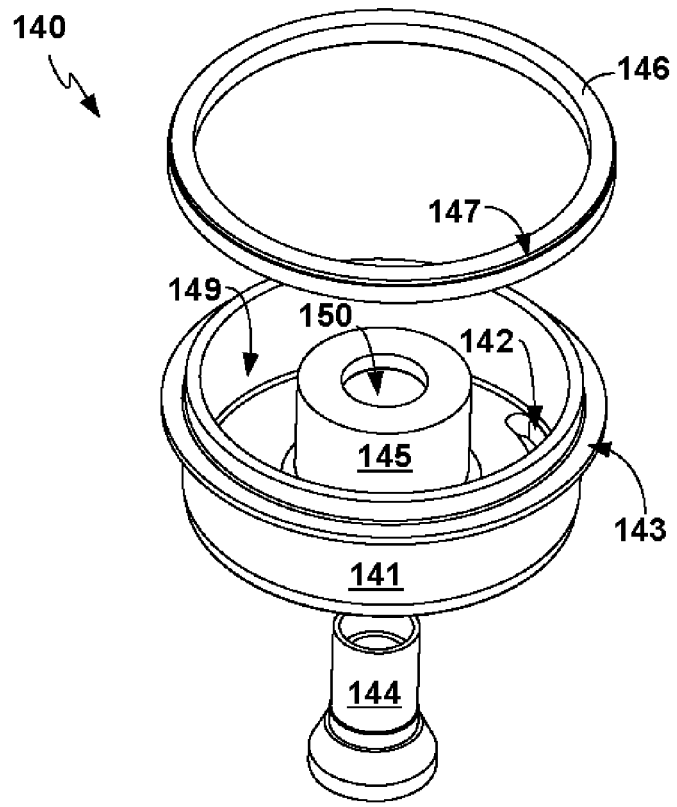

As shown in FIG. 5, cup assembly 140 includes magnetic cup 141, weld ring 146 and sleeve 144. Magnetic cup 141 forms recess 149. Within recess 149, magnetic cup 141 includes protrusion 145. In addition, magnetic cup 141 forms central aperture 150 in protrusion 145, which receives sleeve 144. As an example, sleeve 144 may be interference fit within central aperture 150 or secured within central aperture 150 by other techniques. Weld ring 146 surrounds recess 149 and fits within groove 143 of magnetic cup 141. Weld ring 146 may be interference fit to groove 143 of magnetic cup 141 or secured by other techniques. Magnetic cup 141 comprises a highly magnetic material. The highly magnetic material of magnetic cup 141 efficiently magnetizes in response to current through electromagnetic coil 134. As an example, magnetic cup 141 may comprise a highly magnetic steel alloy. As another example, magnetic cup 141 may comprise a highly magnetic stainless steel alloy such as 430F. However, as highly magnetic materials are generally susceptible to corrosion, magnetic cup 141 is separated from the flow path of fluid being pumped by medical pump 100 to prevent corrosion of magnetic cup 141. As will be discussed in greater detail, weld ring 146 combines with bulkhead 180, barrier plate 130 and sleeve 144 to separate magnetic cup 141 from the flow path.

Electromagnetic coil 134 comprises one or more insulated conductors arranged in a multitude of turns. As examples, electromagnetic coil 134 may comprise a single continuous conductor or more than one conductor electrically connected in series or in parallel. Electromagnetic coil 134 includes flex circuit 136, which provides the electrical connections used to deliver current to electromagnetic coil 134. Within medical pump 100, delivering current to electromagnetic coil 134 magnetizes magnetic cup 141 in order to attract pole 162 for a pump stroke of medical pump 100. Flex circuit 136 fits through hole 142 of magnetic cup 141 and also through hole 183. Hole 183 is formed in the bottom of cup-mounting bay 182 in bulkhead 180 and lines up with hole 142 to receive flex circuit 136.

Barrier plate 130 covers recess 149 to enclose electromagnetic coil 134 within recess 149. Barrier plate 130 forms mating aperture 131, which provides an inner diameter of barrier plate 130. Mating aperture 131 coincides with central aperture 150 of magnetic cup 141. The inner diameter of barrier plate 130 is sealed to sleeve 144, whereas the outer diameter of barrier plate 130 is sealed to weld ring 146. For this reason, the inner diameter of barrier plate 130 may be smaller than the inner diameter of magnetic cup 141, but larger than the inner diameter of sleeve 144. Barrier plate 130 comprises a relatively thin material to provide the best magnetic performance for pump 100 while maintaining sufficient strength and stiffness to isolate electromagnetic coil 134 and magnetic cup 141 from the flow path. For example, barrier plate 130 may have a thickness between about 0.0005 inches to about 0.10 inches. As other examples, barrier plate 130 may have a thickness between about 0.001 inches to about 0.010 inches, a thickness between about 0.001 inches to about 0.005 inches, a thickness of less than about 0.010 inches, a thickness of less than about 0.005 inches, a thickness between about 0.00175 inches to about 0.00225 inches, or a thickness of about 0.002 inches. Barrier plate 130 comprises a biocompatible material. As examples, barrier plate 130 may include a stainless steel alloy, a titanium alloy or other biocompatible material.

Piston/pole subassembly 160 includes piston 166 and pole 162. Piston/pole subassembly 160 is positioned such that piston 166 is located within central aperture 150 of modular pump coil subassembly 120. Spring 132 is located within central aperture 150 adjacent distal end 167 of piston 166. Spring 132 functions to bias piston/pole subassembly 160 away from modular pump coil subassembly 120 such that pole 162 is spaced apart from barrier plate 130. Piston 166 may be interference fit to pole 162 or secured to pole 162 by other suitable techniques. Pole 162 comprises a magnetic material that is attracted to cup assembly 140 to produce a pump stroke. As an example, pole 162 may comprise a stainless steel. Between holes 174 formed in cover 170 and central aperture 150, therapeutic fluid flows through holes 168 in pole 166 as well as through a gap between pole 162 and inner surface of sidewall 176 of cover 170. Because pole 162 is within the fluid flow path, the material of pole 162 should resist corrosion. As an example, pole 162 may comprise a magnetic stainless steel alloy, such as AL29-4. Likewise, piston 166 is also located within the fluid flow path and should also resist corrosion. As an example, piston 166 may comprise sapphire material, which can limit wear between piston and sleeve 144 caused by the pumping action of medical pump 100. As other examples, piston 166 may comprise a metal material, such as a stainless steel or titanium alloy. In some examples, piston/pole subassembly 160 may comprises a unitary component consisting of a single magnetic material such as a stainless steel alloy.

Cover 170 mounts to barrier plate 130 to form an enclosure containing piston/pole subassembly 160 and spring 132. When medical pump 100 is fully-assembled, cover 170 is secured to bulkhead 180 within cup-mounting bay 182. As examples, cover 170 may be interference fit within cup-mounting bay 182 or secured to bulkhead 180 using a weld joint, one or more screws or other techniques. Cover 170 includes holes 174, which allow the therapeutic fluid passing through medical pump 100 to enter the enclosure formed by cover 170 after passing through fluid passageway 186. Cover 170 also includes protrusions 172, which are located on its interior surface adjacent to pole 162. Protrusions 172 serve constrain the motion of piston/pole subassembly 160 thereby limiting the maximum stroke length of a pump stroke. In this manner, the height of protrusion s 172 may be selected to set the stroke length of a pump stroke. As the volume of therapeutic fluid delivered by medical pump 100 per pump stroke directly (pump-stroke volume) relates to the stroke length, the design of medical pump 100 facilitates different pump-stroke volumes simply by changing the height of protrusions 172. The other components of medical pump 100 can be identical for different pump-stroke volumes. However, the pump-stroke volume also depends on the diameter of piston 166 and the inner diameter of sleeve 144, and can also be selected in combination with a stroke length to provide selected pump-stroke volumes.

Piston/pole subassembly 160 actuates within an enclosure between an interior surface of cover 170 and an exterior surface of barrier plate 130. Spring 132 biases piston/pole subassembly 160 away from valve 152 and against protrusions 172 of cover 170. The motion of piston/pole subassembly 160 is driven by electromagnetic coil 134. Specifically, during a pump stroke, current through electromagnetic coil 134 serves to magnetize magnetic cup 141 to attract pole 162. The magnetic attraction force between pole 162 and magnetic cup 141 overcomes the force of spring 132 to create a pumping action of piston 166. The motion of piston 166 forces therapeutic fluid within central aperture 150 and adjacent to distal end 167 of piston 166 through one-way valve 152.

Following a pump stroke, current through electromagnetic coil 134 stops, and spring 132 returns piston/pole subassembly 160 to its original position against cover 170. As spring 132 moves piston/pole subassembly 160, therapeutic fluid flows through a small gap between piston 166 and the inner surface of sleeve 144 to fill the growing space within central aperture 150 adjacent to distal end 167 of piston 166. While some therapeutic fluid could technically flow back though the gap between piston 166 and the inner surface of sleeve 144 during a pump stroke, the speed of a pump stroke combined with the viscosity of the therapeutic fluid allows any amount of therapeutic fluid flowing back though the gap between piston 166 and the inner surface of sleeve 144 during a pump stroke to be negligible.

The size of the gap between piston 166 and the inner surface of sleeve 144 may be selected according to the fluid being pumped through medical pump 100. For example, a higher viscosity fluid may take more time than a lower viscosity fluid to flow through gap between piston 166 and the inner surface of sleeve 144 for a given gap and a given spring force from spring 132. The size of the gap as well as the spring force from spring 132 may be selected to limit backflow during a pump stroke as well as provide a return stroke fast enough for a desired pump stroke rate according to the fluid properties of a particular therapeutic to be pumped through medical pump 100. Generally the gap between piston 166 and the inner surface of sleeve 144 should be selected to prevent backflow while spring 132 should provide a near minimal spring force necessary to accomplish a return stroke fast enough to provide a desired pump stroke rate. These are examples of how medical pump 100 can be customized to suit a particular application with limited modification.

Generally, a return stroke is relatively slow compared to a pump stroke. As an example, a pump stoke may take about 0.01 to 100 milliseconds, whereas a return stroke may take about 0.5 to 20 seconds. As another example, a pump stoke may take about 1 to 10 milliseconds, whereas a return stroke may take about 0.1 to 20 seconds. As another example, a pump stoke may take about 1 to 5 milliseconds, whereas a return stroke may take about 0.5 to 5 seconds. As yet another example, a pump stoke may take about 3 milliseconds, whereas a return stroke may take about 2 seconds. In this manner, the configuration of piston 166 and sleeve 144 acts as a one-way valve during the operation of medical pump 100.

Therapeutic fluid pushed by piston 166 during a pump stroke exits medical pump 100 through one-way valve 152. One-way valve 152 includes three components: disc 154, spring 156 and bonnet 158. Spring 156 functions to bias disc 154 against seat 151 of sleeve 144. Bonnet 158 functions to hold spring 156 in place. As an example, bonnet 158 may be interference fit to sleeve 144. In other examples, bonnet 158 may be attached to sleeve 144 using a weld joint, screws or by other suitable techniques. In yet other examples, valve 152 may be located remotely. In such examples, a sealed fluid passageway, such as a catheter, would connect sleeve 144 and valve 152. Bonnet 158 includes holes that provide fluid passageways through bonnet 158. When one-way valve 152 is closed, disc 154 seals to seat 151 of sleeve 144. The configuration of one-way valve 152 may be referred to as a lift check valve. In other examples, different valve configurations may be used including, but not limited to, ball check valves, diaphragm valves, gate valves and other valves. The design of medical pump 100 allows different valves to be selected for one-way valve 152 as desired according to a particular therapeutic to be pumped through medical pump 100 and the desired pumping characteristics. Generally, one-way valve 152 should be selected to minimize a pressure differential in the fluid flow path at one-way valve 152 while maintaining a fluid seal except during pump strokes.

Figure 6:
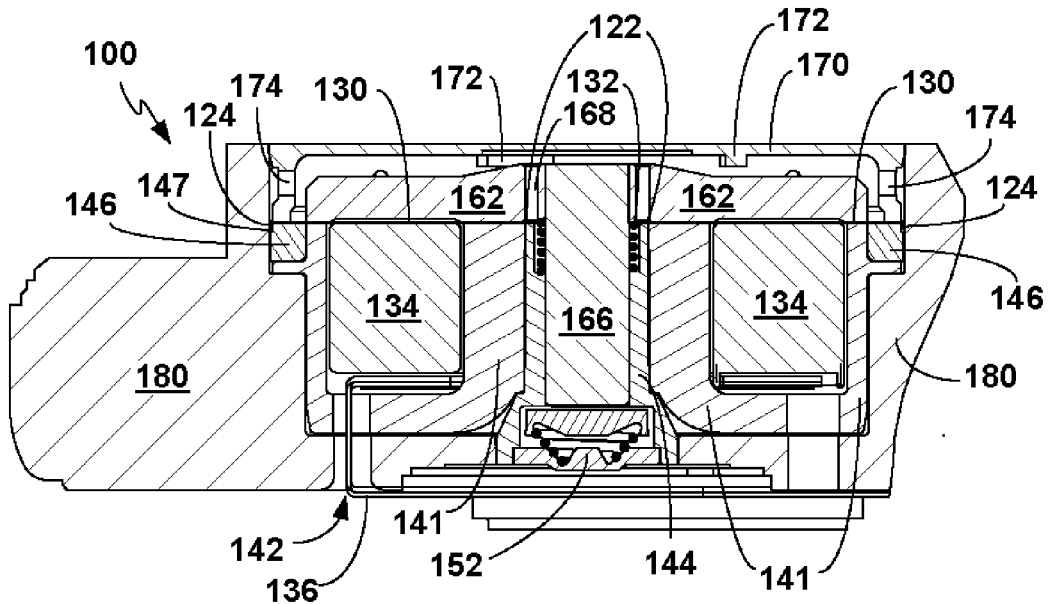

As best shown in FIG. 6, magnetic cup 141 is separated from the flow path of fluid being pumped by medical pump 100. In the manufacture of modular pump coil subassembly 120, the outer diameter of barrier plate 130 is sealed to weld ring 146 to enclose electromagnetic coil 134 within recess 149. In addition, the interior diameter of barrier plate 130 is sealed to sleeve 144. As shown in FIG. 6, barrier plate 130 is sealed to sleeve 144 with a first weld joint, i.e., weld joint 122, and barrier plate 130 is sealed to weld ring 146 with a second weld joint, i.e., weld joint 124. In other examples, barrier plate 130 may be sealed to weld ring 146 and sleeve 144 using other techniques. Weld ring 146 forms notch 147, which is adjacent to an outer perimeter of barrier plate 130. Weld joint 124 is at least partially located within notch 147. As an example, the external diameter of barrier plate 130 may be substantially the same as the inner diameter of notch 147.

The combination of barrier plate 130, sleeve 144, weld ring 146 and weld joints 122, 124 serves to fluidically separate an interior of magnetic cup 141, from an external surface of barrier plate 130, i.e., the surface opposite magnetic cup 141, and thus separate the interior of magnetic cup 141 from fluid being pumped through magnetic pump 100. In addition, modular pump coil subassembly 120 is installed within bulkhead 180 such that weld ring 146 is sealed to cup-mounting bay 182 to fluidically separate an exterior of magnetic cup 141 from an external surface of barrier plate 130, and thus separate the exterior of magnetic cup 141 from fluid being pumped through magnetic pump 100.

As examples, weld ring 146 may be interference fit within bulkhead 180 within cup-mounting bay 182 or sealed to bulkhead 180 with a weld joint or other suitable techniques. In this manner, the design of medical pump 100 completely separates magnetic cup 141 from fluid being pumped through magnetic pump 100. This allows magnetic cup 141 to be formed from a highly magnetic material, such as a highly magnetic steel, which may have a low resistance to corrosion. In contrast, weld ring 146, sleeve 144, barrier plate 130 and bulkhead 180 comprise materials that resist corrosion. Examples of suitable materials include stainless steel and titanium alloys.

The design of cup assembly 140 and, more specifically, weld ring 146, allows modular pump coil subassembly 120 to be assembled separately from bulkhead 180 and tested as a standalone component. In addition, the design of cup assembly 140, including weld ring 146, also allows testing the integrity of seals at the inner and outer diameter of barrier plate 130 before mounting modular pump coil subassembly 120 to bulkhead 180 and electrical testing of electromagnetic coil 134. In one example of a manufacturing process of magnetic pump 100, the integrity of weld joints 122, 124 is tested before potting coil 134 within cup assembly 140 to ensure a tight seal at weld joints 122, 124. Potting involves encasing coil 134 within a non-conductive material within recess 149 by pouring (or forcing) a non-conductive potting material though hole 139 (FIG. 4B) in magnetic cup 141 after barrier plate 130 is sealed to weld ring 146 and sleeve 144. Because the seals separating the interior of magnetic cup 141 from the external surface of barrier plate 130, i.e., weld joints 122, 124 are part of cup assembly 140 and do not include bulkhead 180, the design of modular pump coil subassembly 120 allows coil 134 to be potted within cup assembly 140 before cup assembly 140 is mounted to bulkhead 180 within cup-mounting bay 182. The design of medical pump 100 also allows electrical testing of electromagnetic coil 134 after potting and before mounting modular pump coil subassembly 120 to bulkhead 180.

In general, potting includes allowing the potting material to "set-up" or harden after filling the remaining space within recess 149 within the potting material. As examples, a potting material may be an epoxy or a polymer. Potting coil 134 within cup assembly 140 can take a significant amount of time to allow the potting material to harden. Depending on the potting material, potting can take between about 1 to 24 hours. As another example, potting can take about between about 2 to 12 hours. As another example, potting can take about 8 hours. Because the potting process takes a significant amount of time, separating potting process from bulkhead 180 streamlines the assembly of medical pump 100.

In addition, during the manufacturing of a plurality of medical pumps 100, some of weld joints 122, 124 will not form proper seals. In such instances, the faulty cup assembly 140 may be removed from the assembly process. In contrast, in an alternative design in which the outer diameter of barrier plate 130 is sealed directly to cup-mounting bay 182 of bulkhead 180, e.g., using a weld joint, instead of indirectly via weld ring 146, testing the integrity of the seal between barrier plate 130 and cup-mounting bay 182 could only be performed after mounting magnetic cup 141 within cup-mounting bay 182. In such an alternative design, in the event of a bad seal, the entire assembly, including bulkhead 180, would have to be removed from the assembly process. In this manner, the design of medical pump 100 provides the advantage of facilitating a manufacturing process that does not waste a bulkhead 180 in the event of a bad seal at one of weld joints 122, 124.

While numerous techniques may be suitable to manufacture cup assembly 140, the following techniques may be included in the manufacture cup assembly 140. In each stage of the following description, components are referred to using the same names as these components have in a full-assembled medical pump 100, even though such components may not yet include each its associated features provided during the previous description of medical pump 100.

Central aperture 150 is machined in magnetic cup 141 to receive sleeve 144; likewise, sleeve 144 is bored to accept piston 166. Next, sleeve 144 is interference fit within central aperture 150 of magnetic cup 141. Then, valve seat 151 is finish-machined to accept valve 152, and the bore of sleeve 144 is also finish-machined to piston 166. Following this step, the combined magnetic cup 141/sleeve 144 is passivated using acid and vacuum-baked. Vacuum-baking may limit the occurrence of corrosion at the interface between magnetic cup 141 and sleeve 144 and the interface between magnetic cup 141 and weld ring 146 during future heat treatment processes. For example, such corrosion may be caused by particles left behind by tooling used in the finish machining. Following the vacuum-baking, the combined magnetic cup 141/sleeve 144 is heat treated. The heat treatment forms a hard titanium-oxide layer on sleeve 144, which improves the wear resistance of sleeve 144 to limit wear caused by the motion of piston 166.

Next, groove 143 is machined in magnetic cup 141, and weld ring 146 is machined from a titanium alloy to fit groove 143. Weld ring 146 is then interference fit within groove 143 of magnetic cup 141. Then, cup assembly 140 is finished-machined. Finish machining including machining notch 147 in weld ring 146 as well as forming recess 149 within magnetic cup 141. Forming recess 149 within magnetic cup 141 includes leaving protrusion 145 in place. The finish machining also includes facing-off the upper surfaces of magnetic cup 141, including protrusion 145, sleeve 144 and weld ring 146 to ensure these surfaces are substantially coplanar. It is useful to ensure that the upper surfaces of magnetic cup 141 are substantially coplanar to improve the likelihood that weld joints 122, 124 will form proper seals with barrier plate 130. Following this step, the cup assembly 140 is again passivated with acid and vacuum-baked. One-way valve 152 is then seated in valve seat 151 of sleeve 144. The forgoing description provides an example of techniques that may be included in the manufacture cup assembly 140. Other techniques and combinations of techniques may be used in the manufacture of cup assembly 140.

Modular pump coil subassembly 120 can be electrically and seal tested as a standalone component. This limits manufacturing costs by detecting defective pump components before installation of pump coil subassembly 120 within a bulkhead. In addition, modular pump coil subassembly 120 allows for faster assembly because potting of the pump coil occurs prior to the assembly line process, further limiting manufacturing costs by reducing the time and space required for the assembly of an IMD including pump coil subassembly 120.

FIGS. 7-10 illustrate components of modular medical pump 200, in accordance with another example. Medical pump 200 facilitates pump operation testing prior to assembling the modular medical pump in a bulkhead, i.e., testing of modular pump 218 as a standalone component. Medical pump 200 includes modular pump 218 with cover 270, which includes filter element 276 (FIG. 9), and bulkhead 280. In many respects, medical pump 200 is similar to medical pump 100. For example, many of the components described with respect to medical pump 100 are also suitable for medical pump 200. These components are numbered the same in FIGS. 7-10 with respect to medical pump 200 as in FIGS. 3-6 with respect to medical pump 100. For brevity, such components are described in little, if any, detail with respect to medical pump 200.

Like medical pump 100, medical pump 200 may be part of an IMD, such as IMD 12 (FIG. 1). In contrast to medical pump 100, medical pump 200 includes a modular pump, modular pump 218, which is mechanically and electrically functional without bulkhead 280. Medical pump 200 also includes bulkhead 280. Modular pump 218 includes cup assembly 140, coil 134, barrier plate 130, spring 132, piston/pole subassembly 160, cover 270 and one-way valve 152.

Figure 7:
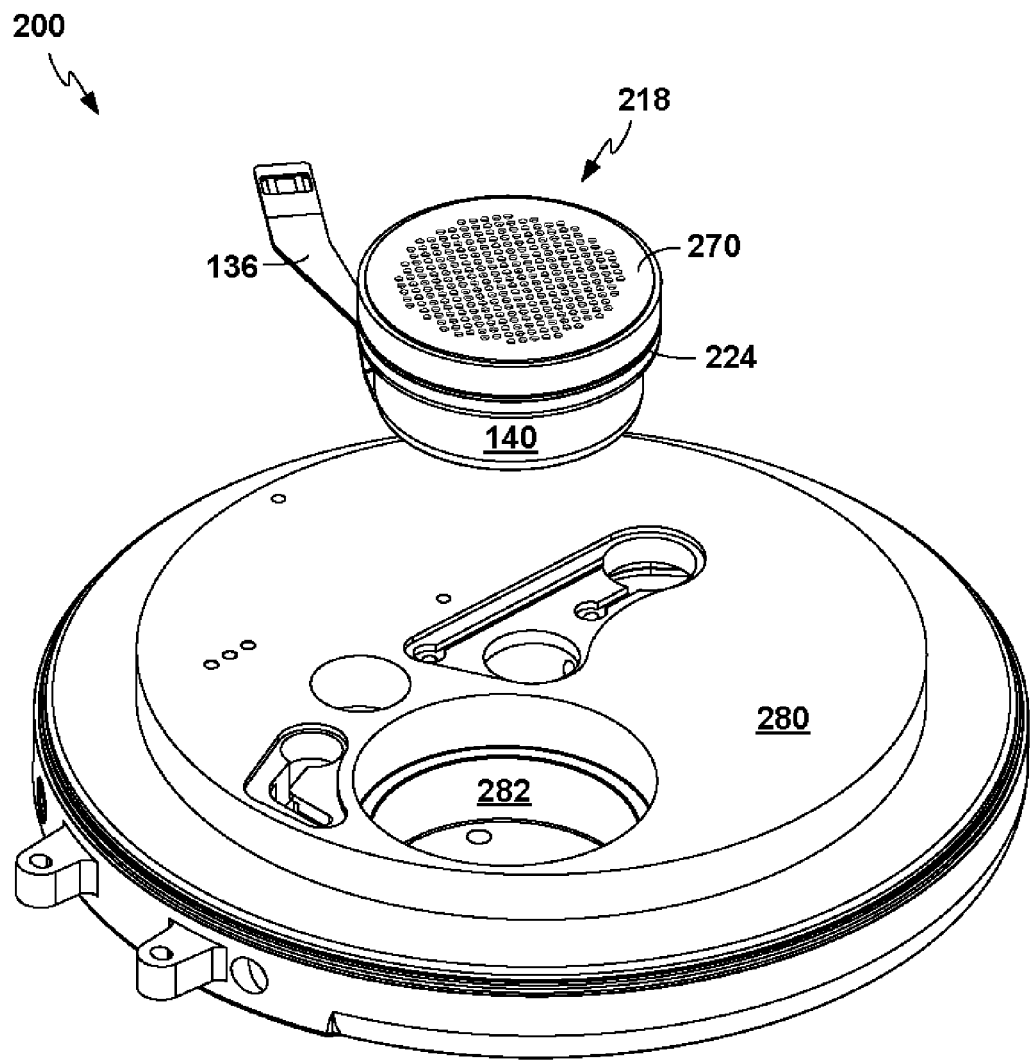
FIGS. 7-10 illustrate components of an exemplary modular medical pump that facilitates pump operation testing prior to assembling a modular pump in a bulkhead.
Figure 8A:
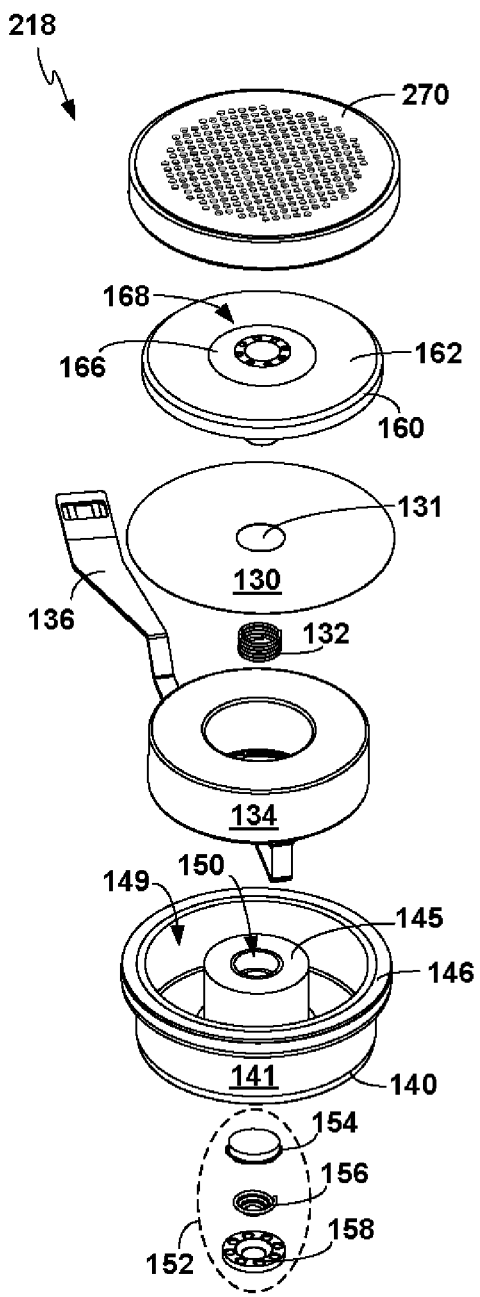
Figure 8B:
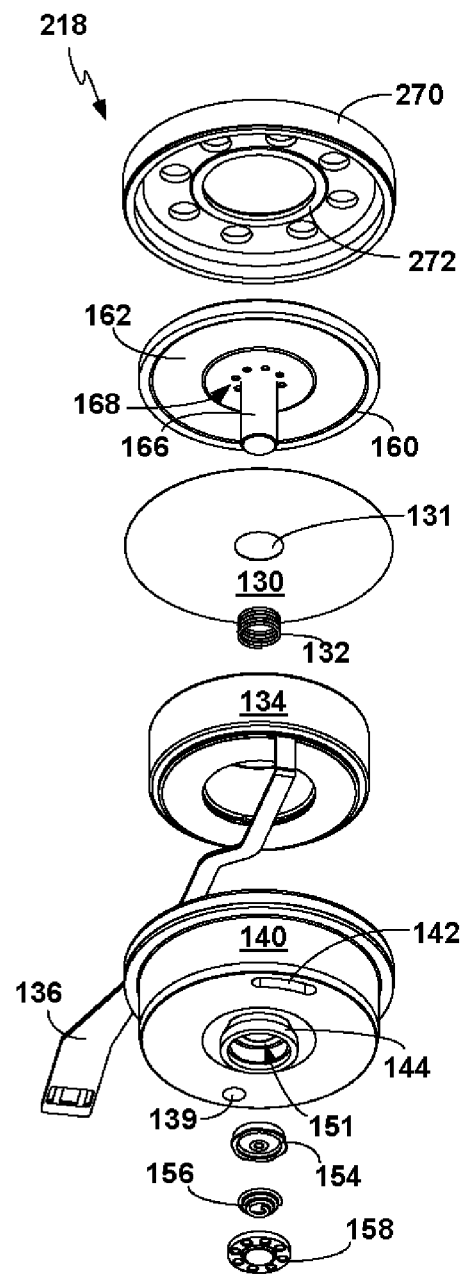

As shown in FIG. 7, bulkhead 280 includes cup-mounting bay 282 to receive modular pump 218. In contrast to bulkhead 180 (FIG. 3), bulkhead 280 does not include a filter-mounting bay. Instead, cover 270 of medical pump 200 includes an integrated filter. As with bulkhead 180, bulkhead 280 comprises a biocompatible material. As examples, bulkhead 280 may include a stainless steel alloy, a titanium alloy or other biocompatible material.

Figure 9:
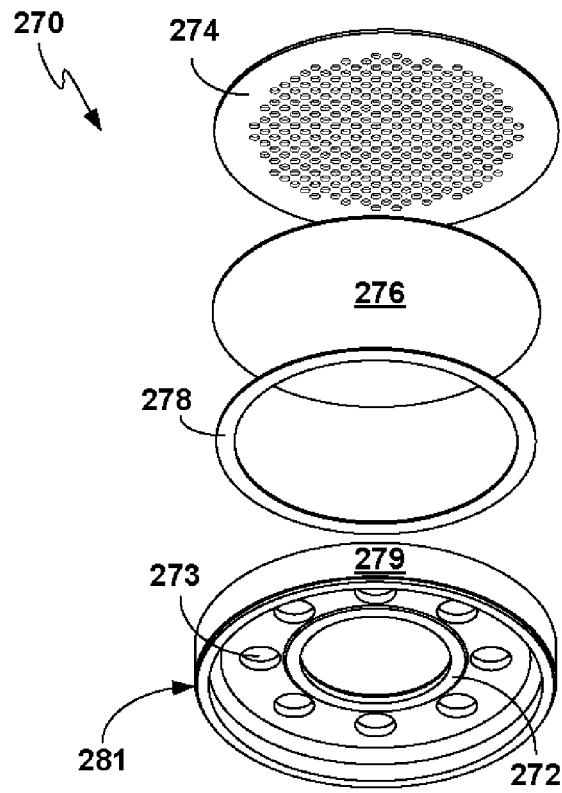

As shown in FIG. 9, cover 270 includes perforated screen 274, filter element 276, gasket 278 and base 279. Gasket 278 forms a seal between filter element 276 and base 279 to prevent any therapeutic fluid flowing through modular pump 218 (FIG. 7) from bypassing filter element 276. Perforated screen 274 serves to compress filter element 276 and gasket 278 to provide a seal between filter element 276 and gasket 278 as well as a seal between gasket 278 and base 279. As the components of cover 270 are within the flow path of fluid being pumped by medical pump 200, the components of cover 270 comprise biocompatible materials. As examples, perforated screen 274 and base 279 may comprise a stainless steel, titanium alloy or other suitable material. As another example, perforated screen 274 and base 279 may comprise a polymer, a stainless steel or other suitable material. In addition, gasket 278 may comprise a deformable material, such as a polymer, silicon rubber or other suitable material.

Holes 273 provide the fluid flow path through base 279. In addition, base 279 includes protrusion 272, which serves constrain the motion of piston/pole subassembly 160 thereby limiting the maximum stroke length of a pump stoke. As discussed with respect to protrusions 172 in medical pump 100, the height of protrusion 272 may be selected to set the stroke length of a pump stroke of medical pump 200.

Figure 10:
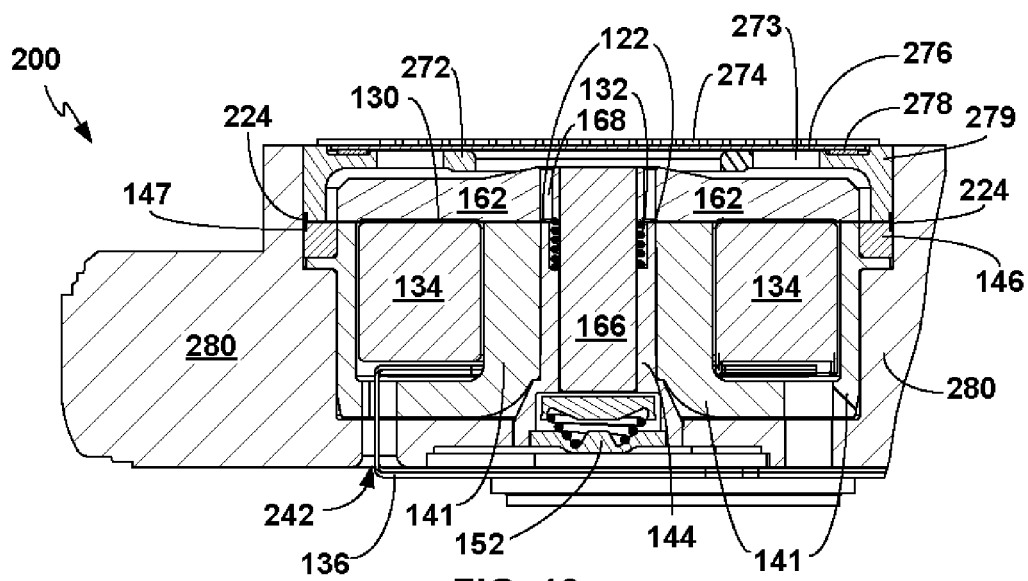

As best shown in FIG. 10, magnetic cup 141 is separated from the flow path of fluid being pumped by medical pump 200. In the manufacture of modular pump 218, the interior diameter of barrier plate 130 is first sealed to sleeve 144. Then, the outer diameter of barrier plate 130 is sealed to weld ring 146 to enclose electromagnetic coil 134 within recess 149. As shown in FIG. 10, barrier plate 130 is sealed to sleeve 144 with a first weld joint: weld joint 122, and barrier plate 130 is sealed to weld ring 146 with a second weld joint: weld joint 224. However, in contrast to medical pump 100, the second weld joint, weld joint 224 also attaches cover 270 to barrier plate 130 and weld ring 146. Because cover 270 is placed over barrier plate 130 prior to forming weld joint 224, weld joint 224 can not interfere with the placement of cover 270 against barrier plate 130. In contrast, in medical pump 100, weld joint 124 (FIG. 6) could potentially interfere with the placement of cover 270 against barrier plate 130. The location of cover 270 is important at least because protrusions 272 serve to set the stroke length of a pump stroke of medical pump 200.

Weld ring 146 forms notch 147, which is adjacent to an outer perimeter of barrier plate 130. Likewise, base 279 of cover 270 forms notch 281, which is adjacent to notch 147 in weld ring 146. Weld joint 224 is partially located within notch 147, and weld joint 224 is also partially located within notch 281. As an example, the external diameter of barrier plate 130 may be substantially the same as the inner diameter of notch 147 and the inner diameter of notch 281. The combination of barrier plate 130, sleeve 144, weld ring 146 and weld joints 122, 224 serves to fluidically separate an interior of magnetic cup 141 from an external surface of barrier plate 130, and thus separate the interior of magnetic cup 141 from fluid being pumped through magnetic pump 200. In addition, modular pump 218 is installed within bulkhead 280 such that weld ring 146 is sealed to cup-mounting bay 282 to fluidically separate an exterior of magnetic cup 141 from an external surface of barrier plate 130, and thus separate the exterior of magnetic cup 141 from fluid being pumped through magnetic pump 200. As examples, weld ring 146 may be interference fit within bulkhead 280 within cup-mounting bay 282 or sealed to bulkhead 280 with a weld joint or other suitable techniques. In this manner, the design of medical pump 200 completely separates magnetic cup 141 from fluid being pumped through magnetic pump 200.

As discussed with respect to medical pump 100, the design of medical pump 200 allows potting of coil 134 to be performed separately from the assembly of components to bulkhead 280, which streamlines the manufacture of medical pump 200. The design of medical pump 200 also allows seal integrity testing of weld joints 122, 224. Furthermore, modular pump 218 can be electrically, mechanically and seal tested as a standalone component, i.e., prior to installation in bulkhead 280. This additional testing further ensures the functionality of the components of medical pump 200 prior to final assembly in bulkhead 280. One additional advantage of the design of medical pump 200 as compared to medical pump 100 is that a higher class cleanroom, i.e., a dirtier cleanroom, may be used during the assembly processes including bulkhead 280. For example, assembly of medical pump 100 and modular pump 218 may be performed in an International Organization for Standardization (ISO) 14644-1 Class 5 (FED STD 209E Class 100) cleanroom, whereas assembly of medical pump 200 may be performed in an ISO 14644-1 Class 7 (FED STD 209E Class 10,000) cleanroom.

Figure 11:
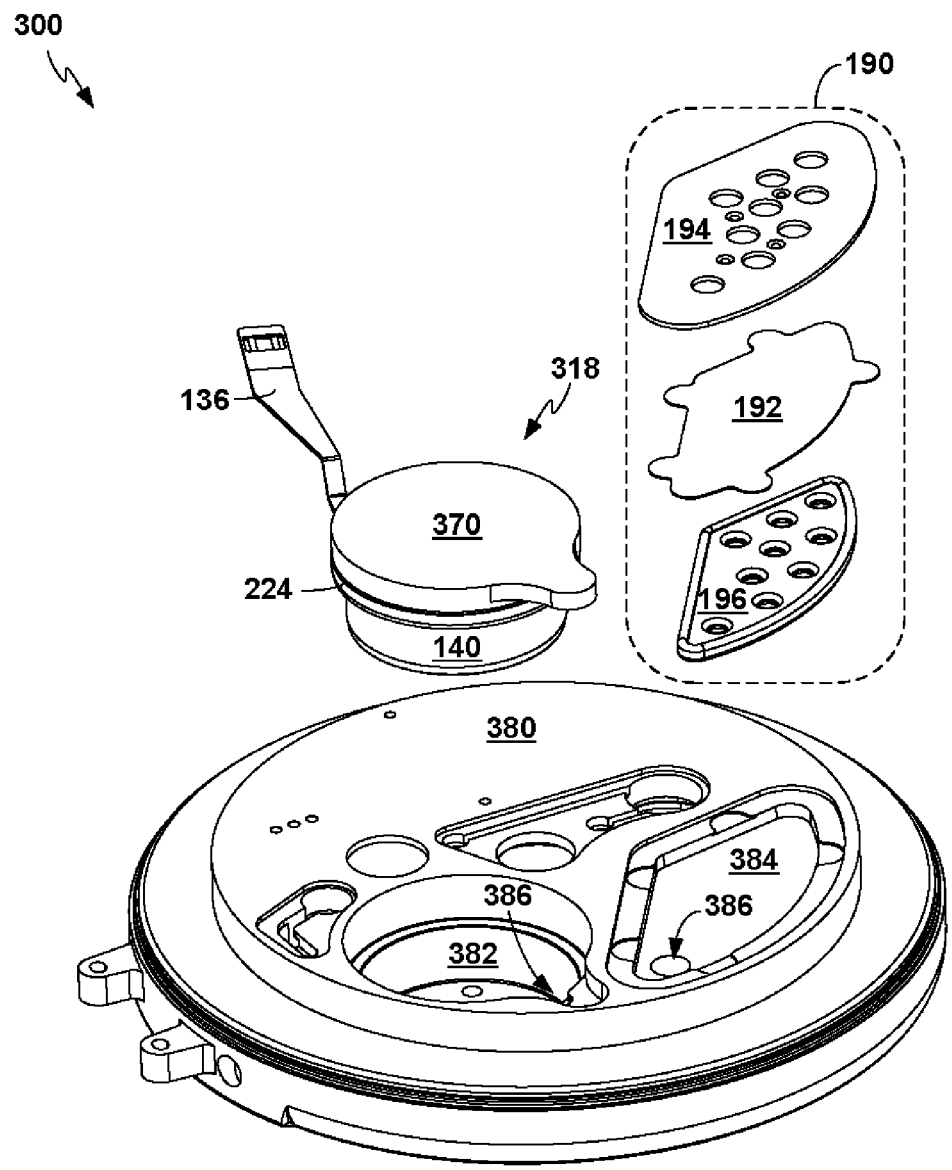
FIGS. 11, 12A and 12B illustrate components of an exemplary modular medical pump that facilitates pump operation testing prior to assembling the modular pump in a bulkhead.
Figure 12A:
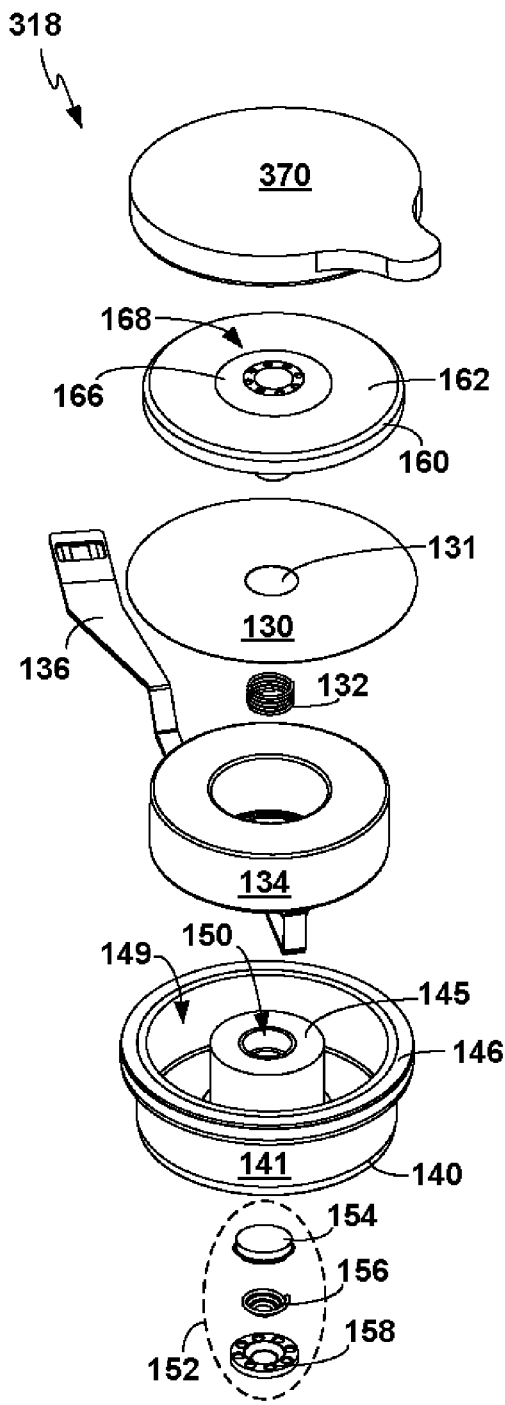
Figure 12B:
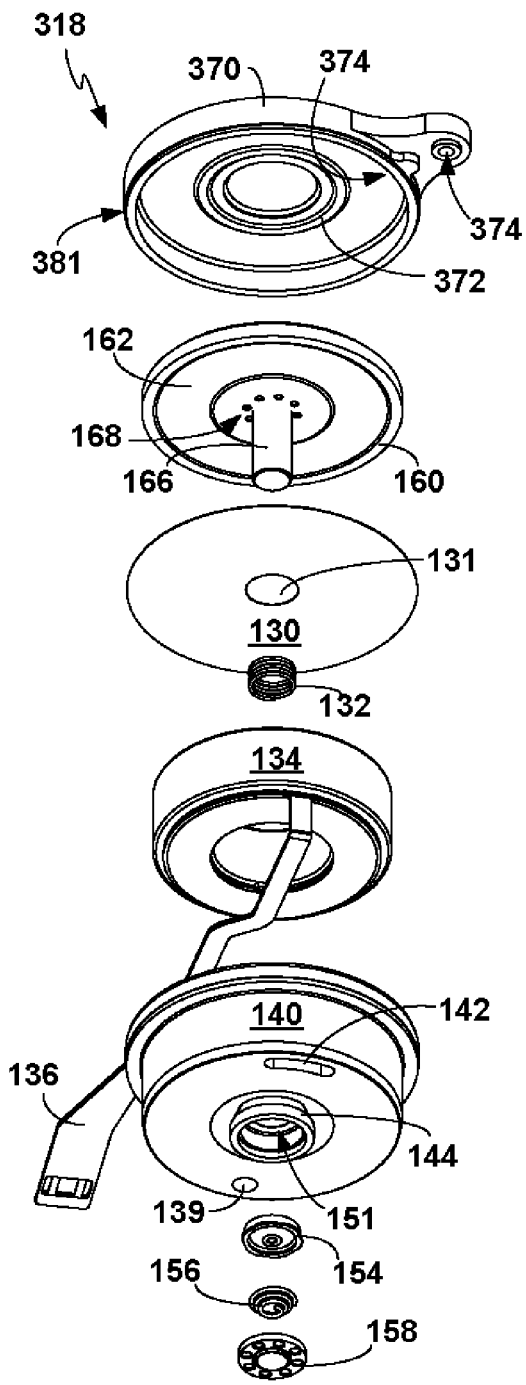

FIGS. 11-12B illustrate components of modular medical pump 300. Medical pump 300 is substantially similar to medical pump 200, with the exception that cover 370 does not include an integrated filter element. The design of medical pump 300 facilitates pump operation testing of the modular medical pump as a standalone component, i.e., prior to assembling the modular medical pump in a bulkhead. Medical pump 300 includes cover 370, filter element 190 and bulkhead 380. In many respects, medical pump 300 is similar to medical pumps 100, 200. For example, many of the components described with respect to medical pumps 100, 200 are also suitable for medical pump 300. For brevity, such components are described in little, if any, detail with respect to medical pump 300.

Medical pump 300 may be part of an IMD, such as IMD 12 (FIG. 1). Medical pump 300 includes modular pump 318, filter element 190 and bulkhead 380. Modular pump 318 includes cup assembly 140, coil 134, barrier plate 130, spring 132, piston/pole subassembly 160, cover 370 and one-way valve 152.

As shown in FIG. 11, bulkhead 380 includes cup-mounting bay 382 to receive modular pump 318 and filter-mounting bay 384 to receive filter 190. Fluid passageway 386 connects cup-mounting bay 382 to filter-mounting bay 384. Bulkhead 380 comprises a biocompatible material. As examples, bulkhead 380 may include a stainless steel alloy, a titanium alloy or other biocompatible material. Cover 370 also comprises a biocompatible material such as a stainless steel, titanium alloy or other suitable material.

In contrast to cover 270 of modular pump 218, cover 370 is a unitary component. Fluid passageway 374 in cover 370 directs fluid from fluid passageway 386 in bulkhead 380 into modular pump 318. Cover 370 includes protrusion 372, which serves to constrain the motion of piston/pole subassembly 160 thereby limiting the maximum stroke length of a pump stoke. As discussed with respect to protrusions 172 in medical pump 100, the height of protrusion 372 may be selected to set the stroke length of a pump stroke of medical pump 300. Cover 370 also forms notch 381, which is adjacent to notch 147 in weld ring 146. A weld joint sealing weld ring 146, the outer diameter of barrier plate 130, and cover 370 is partially located within notch 147 and also partially located within notch 381. As an example, the external diameter of barrier plate 130 may be substantially the same as the inner diameter of notch 147 and the inner diameter of notch 381.

As discussed with respect to medical pump 100, the design of medical pump 300 allows potting of coil 134 to be performed separately from the assembly of components to bulkhead 380, which streamlines the assembly of medical pump 300. The design of medical pump 300 also allows seal integrity testing and electrical and mechanical testing of pump 300 as a standalone component. This testing further ensures the functionality of the components of medical pump 300 prior to final assembly in bulkhead 380. In addition, as discussed with respect to medical pump 200, a higher class clean room, i.e., dirtier, may be used during assembly processes including bulkhead 380 than for assembly of modular pump 318.

Figure 13:
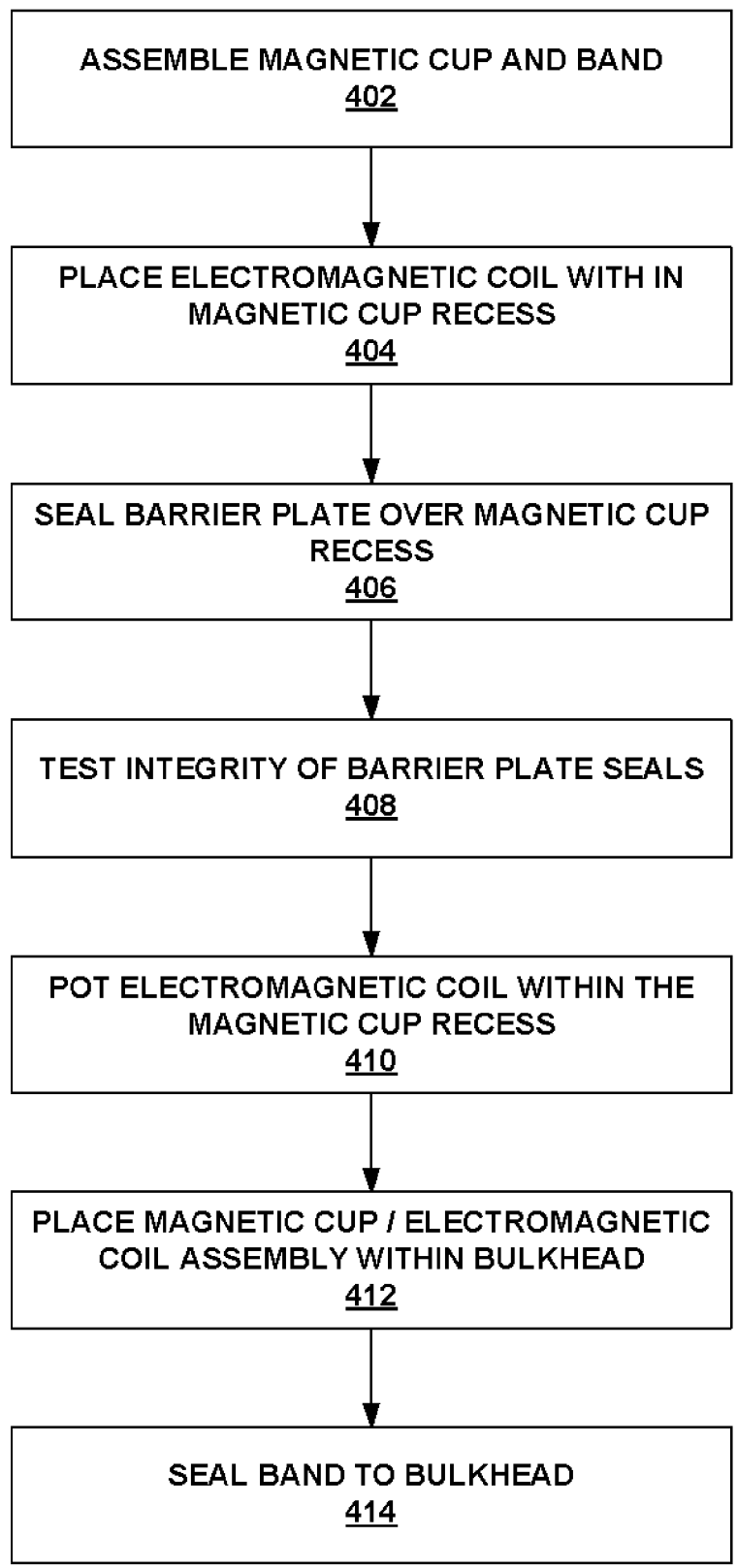
FIG. 13 is a flowchart illustrating techniques for manufacturing a medical pump.

FIG. 13 is a flowchart illustrating techniques for manufacturing a medical pump. For clarity, the techniques shown in FIG. 13 are described with respect to medical pump 100. Some of the assembly steps may be automated whereas other steps may be performed manually. First, magnetic cup 141 and weld ring 146 are assembled (402). For example, weld ring 146 may be assembled to magnetic cup 141 by interference fit. Next, electromagnetic coil 134 is placed within recess 149 circumscribing protrusion 145 (404). Barrier plate 130 is then sealed to weld ring 146 to enclose the electromagnetic coil 134 within recess 149 (406), and integrity of the seals of barrier plate 130 is tested (408). Sealing barrier plate 130 to weld ring 146 and to sleeve 144 fluidically separates an interior of magnetic cup 141 from an external surface of barrier plate 130. Next, electromagnetic coil 134 is potted within magnetic cup recess 149 (410). Finally, modular pump coil subassembly 120 is placed within cup-mounting bay 182 of bulkhead 180 (412) and weld ring 146 is sealed to bulkhead 180 (414) to fluidically separate an exterior of magnetic cup 141 from an external surface of barrier plate 131.

Figure 14:
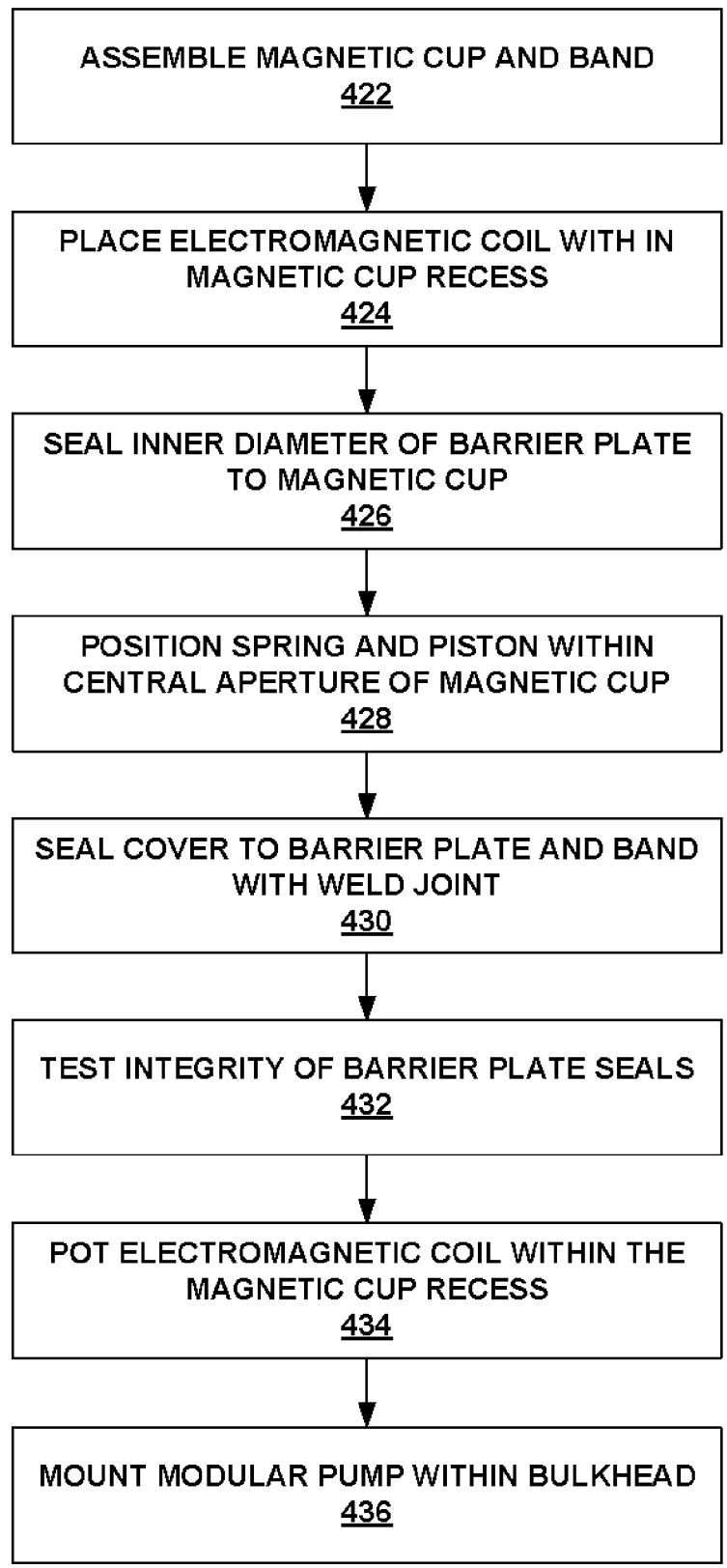
FIG. 14 is a flowchart illustrating techniques for manufacturing a medical pump including a pump module.

FIG. 14 is a flowchart illustrating techniques for manufacturing a medical pump including a pump module. For clarity, the techniques shown in FIG. 14 are described with respect to medical pump 200. First, magnetic cup 141 and weld ring 146 are assembled (422). For example, weld ring 146 may be assembled to magnetic cup 141 by interference fit. Next, electromagnetic coil 134 is placed within recess 149 circumscribing protrusion 145 (424). The inner diameter of barrier plate 130 is then sealed to sleeve 144 of cup assembly 140, e.g., with weld joint 122 (426). Spring 132 and piston 166 of piston/pole subassembly 160 are positioned within central aperture 150 (428). Cover 270 is positioned over barrier plate 130 and piston/pole subassembly 160. The outer diameter of barrier plate 130 is then sealed to weld ring 146 and cover 270 with weld joint 224 (430), and integrity of the seals of barrier plate 130 is tested (432). In other examples, such as medical pump 500 in FIG. 16, two separate weld joints 523, 524 may be used to seal the outer diameter of a barrier plate 130 to a weld ring 146 and a cover 570 (430). Sealing barrier plate 130 to weld ring 146 and to sleeve 144 fluidically separates an interior of magnetic cup 141 from an external surface of barrier plate 130. Next, electromagnetic coil 134 is potted within recess 149 (434). Optionally, modular pump 218 may then be electrically, mechanically and seal tested as a standalone component. Finally, modular pump 218 is mounted with cup-mounting bay 282 of bulkhead 280 (436), and weld ring 146 is sealed to bulkhead 180 to fluidically separate an exterior of magnetic cup 141 from an external surface of barrier plate 131.

Medical pumps designs having a fixed stroke length, such as medical pumps 100, 200, 300 may be easier to manufacture and more reliable than medical pumps with adjustable stroke lengths. As referred to herein, medical pumps having a fixed stroke length, is a medical pump in which the stroke length of a piston of the pump is not adjustable in a manner that could account for variability in the manufacture of a plurality of substantially identical medical pumps, e.g., a series of medical pumps manufactured according to the same design and specifications. However, in contrast to medical pumps with adjustable stroke lengths, individual medical pumps with fixed stroke lengths can not be calibrated to account for variability in the manufacturing process to ensure that each of a plurality of substantially identical pumps provide the same volume of fluid delivered per pump stroke. As referred to in this disclosure, pumps are considered to be substantially identical pumps if built according to the same design and specifications, such as a series of pumps manufactured using interchangeable parts on the same assembly line. In some medical pump applications, such as the delivery of therapeutic fluids, the variability in volume of fluid delivered per pump stroke among a plurality of substantially identical pumps is not precise enough to provide optimal patient treatment using the medical pumps. For this reason, it may be useful to calibrate a patient therapy program to a measured volume of fluid delivered per pump stroke for the medical pump in a plurality of substantially identical pumps being controlled by the patient therapy program. In other words, a patient therapy program may be slightly adjusted to deliver desired therapy while compensating for slight differences between different substantially identical pumps.

Figure 15:
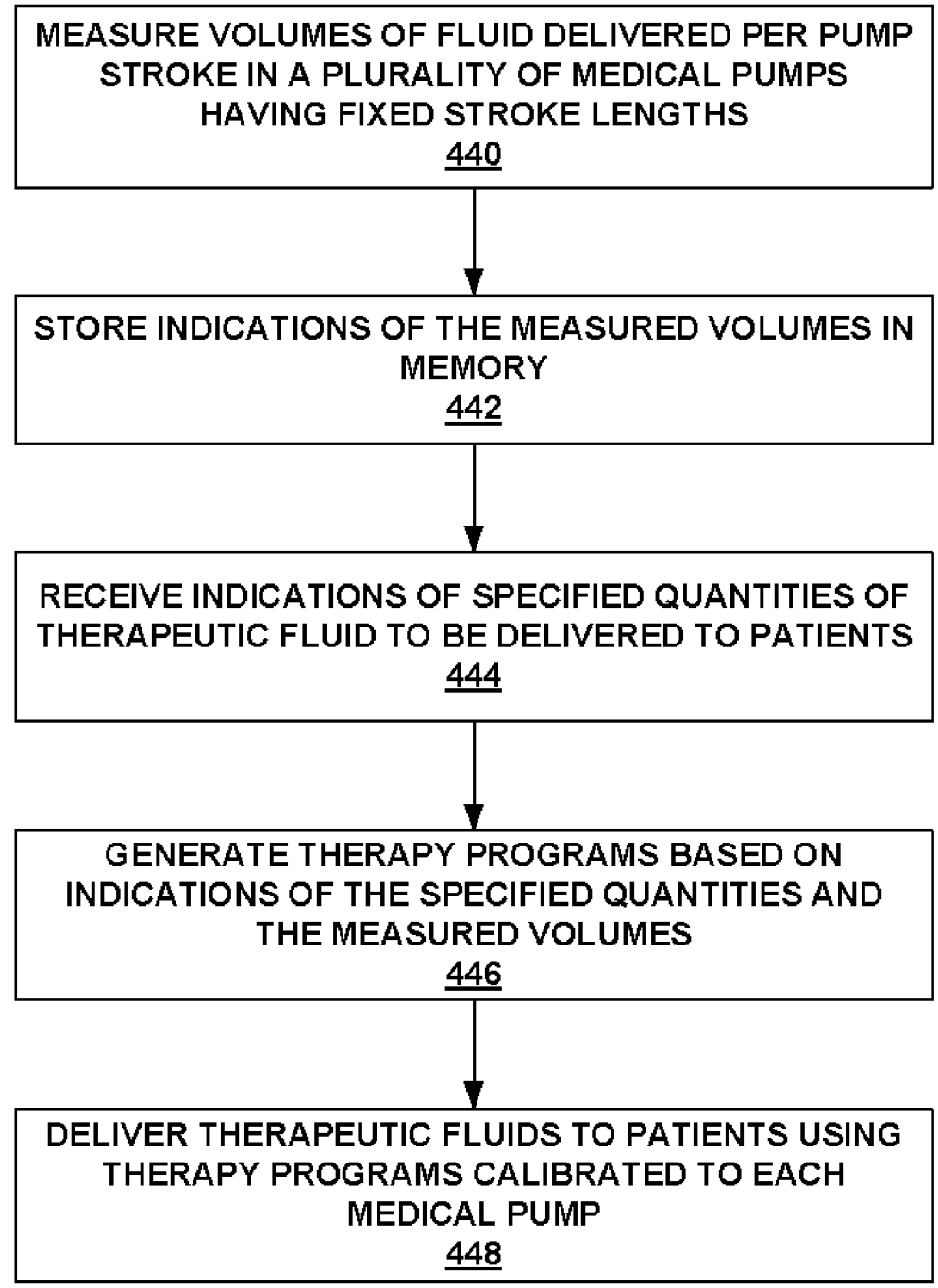
FIG. 15 is a flowchart illustrating techniques for delivering specified quantities of therapeutic fluid to patients using medical pumps with fixed stroke lengths.

FIG. 15 is a flowchart illustrating techniques for delivering specified quantities of therapeutic fluid to patients using medical pumps with fixed stroke lengths. For clarity, the techniques shown in FIG. 15 are described with respect to IMD 12, programmer 20 and medical pumps 100, 200, 300.

First, following the manufacture or assembly of a plurality of medical pumps having fixed stroke lengths, a volume of fluid delivered per pump stroke is measured for each of the medical pumps (440). Medical pumps 100, 200, 300 are examples of medical pumps with fixed stroke lengths. In addition, pump modules 218, 318 are also considered medical pumps with fixed stroke lengths as pump modules 218, 318 provide the pumping function of medical pumps 200, 300. Measuring a volume of fluid delivered per pump stroke in a medical pump may include connecting the medical pump to a power source, pumping a fluid with the medical pump using a known number of pumping strokes, and measuring (e.g., by mass or volume) the pumped fluid to determine the volume of fluid delivered per pump stroke of the medical pump. The volume of fluid delivered may be measure automatically as part of the assembly process, or manually, either as part of the assembly process, or by a clinician prior to operation of a medical pump in conjunction with a patient.

Indications of the measured volumes are stored in memory (442). An indication of a measured volume could be entered manually, e.g., into a user-interface of programmer 20 or automatically by an instrument used to measure the volumes. As examples, the memory could be included in an IMD including the medical pump, such as memory 40 in IMD 12. As another example, the memory could be a memory of a programmer such as programmer 20.

As other examples, the memory could be a removable data storage media, such as a compact disc, memory card, magnetic disk, or the like. In some cases, the information may be stored as part of a computer database that includes indications of volumes of fluid delivered per pump stroke for plurality of substantially identical medical pumps. The stored indication of volume of fluid per pump stroke for a medical pump is stored in a manner that associates the medical pump with the stored indication. For example, the indication may be stored in a memory associated with the medical pump and/or the indication may be stored with a unique identifier, e.g., a serial number, of the medical pump to associate the medical pump with the stored indication.

Following implantation of an IMD including the medical pump in a patient, the stored indication of volume of fluid delivered can be used to calibrate a therapy program for the delivery of a therapeutic fluid to the patient. For example, for each medical pump, a programmer, such as programmer 20, may receive an indication of a specified quantity of therapeutic fluid to be delivered to a patient from a user (444). In different examples, the user may be the patient or a clinician. The specified quantity of therapeutic fluid may be defined as a volume, as a flow-fate, according to one or more physiological characteristics of the patient or by other means.

Next, for each medical pump, a processor accesses the indication of volume of fluid per pump stroke for a medical pump stored in memory and generates a therapy program based on the indication of volume of fluid delivered per pump stroke and the specified quantity of therapeutic fluid to be delivered to the patient (446). The processor can be located in an IMD including the medical pump, within a programmer associated with the medical pump or within a remote device in communication with therapy system 10.

As an example, the processor may be processor 38 of IMD 12. In such an example, IMD 12 may receive the specified quantity of therapeutic fluid to be delivered to the patient from programmer 20 and generate the therapy program based on the indication of volume of fluid per pump stroke automatically. Such a process may occur automatically and without the knowledge of a user who provided the specified quantity of fluid to be delivered.

As another example, the processor may be part of controller 20. In such an example, controller 20 may then issue instructions to IMD 12 to deliver the therapeutic fluid with the equivalent quantity of pump strokes rather than directly specifying a quantity of fluid delivered in the instructions to IMD 12. Again, such a process may occur automatically and without the knowledge of a user who provided the specified quantity of fluid to be delivered.

After generation of the therapy programs, each of the medical pumps deliver a specified quantity of therapeutic fluid to a patient using a therapy program calibrated to that particular medical pump based on a volume of fluid delivered per pump stroke measured from that particular medical pump (448).

In the manner, the specified quantities of therapeutic fluid to be delivered are converted to equivalent quantities of pump strokes based on indications of the volume of fluid delivered per pump stroke stored in a memory to account for variability in the manufacture of a plurality of substantially identical medical pumps. Generally, the techniques of FIG. 15 are repeated for each of the plurality of substantially identical medical pumps.

Figure 16:
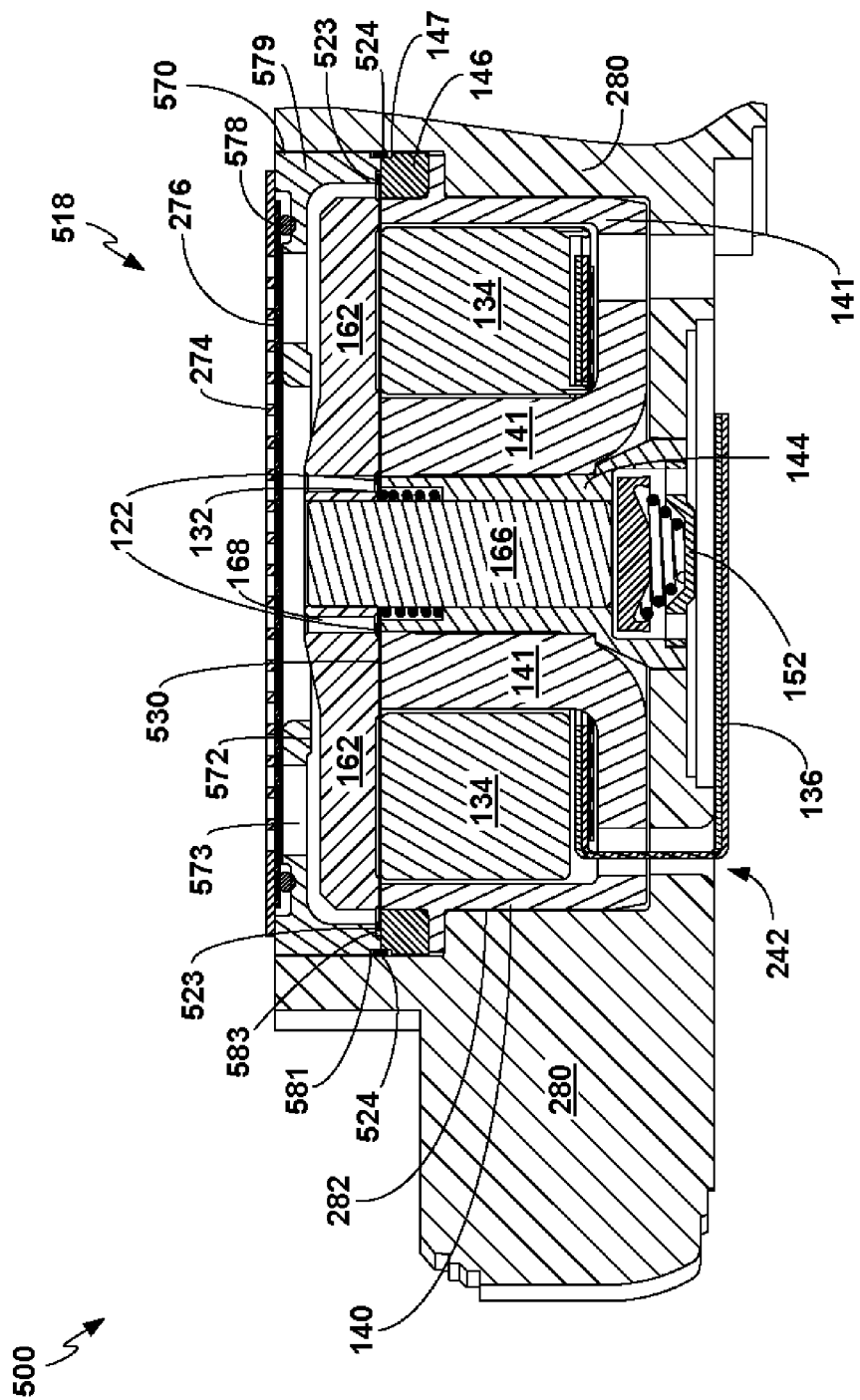
FIG. 16 is illustrates components of an exemplary modular medical pump that facilitates pump operation testing prior to assembling the modular pump in a bulkhead.

FIG. 16 illustrates components of modular medical pump 500, in accordance with another example. Medical pump 500 facilitates pump operation testing of modular medical pump 518 as a standalone component, i.e., prior to assembly of modular medical pump 518 in bulkhead 280. Like medical pump 200, medical pump 500 may be part of an IMD, such as IMD 12 (FIG. 1). Medical pump 500 includes modular pump 518 and bulkhead 280. Modular pump 518 includes cup assembly 140, coil 134, barrier plate 530, spring 132, piston/pole subassembly 160, cover 570 and one-way valve 152.

Medical pump 500 is substantially similar to medical pump 200. One exception is that the functionality of weld joints 523, 524 in medical pump 200 is provided by two separate weld joints 523, 524 in medical pump 500. In addition, barrier plate 530 has a smaller outer diameter than barrier plate 530 to accommodate weld joint 523, and base 579 of cover 570 includes notch 583 to accommodate weld joint 523.

Cover 570 includes perforated screen 274, filter element 276, gasket 578 and base 579. Gasket 578 forms a seal between filter element 276 and base 579 to prevent any therapeutic fluid flowing through modular pump 518 from bypassing filter element 276. Perforated screen 274 serves to compress filter element 276 and gasket 578 to provide a seal between filter element 276 and gasket 578 as well as a seal between gasket 578 and base 579. As the components of cover 570 are within the flow path of fluid being pumped by medical pump 200, the components of cover 570 comprise biocompatible materials. As examples, perforated screen 274 and base 579 may comprise a stainless steel, titanium alloy or other suitable material. As another example, perforated screen 274 and base 579 may comprise a polymer, a stainless steel or other suitable material. In addition, gasket 578 may comprise a deformable material, such as a polymer, silicon rubber or other suitable material. Gasket 578 has a round cross-section, which in contrast to gasket 278 of cover 270, which has a rectangular cross-section. However, gasket 278 and gasket 578 provide equivalent functionality.

Holes 573 provide the fluid flow path through base 579. In addition, base 579 includes protrusion 572, which serves constrain the motion of piston/pole subassembly 160 thereby limiting the maximum stroke length of a pump stoke. As discussed with respect to protrusions 172 in medical pump 100, the height of protrusion 572 may be selected to set the stroke length of a pump stroke of medical pump 200.

Magnetic cup 141 is separated from the flow path of fluid being pumped by medical pump 500. In the manufacture of modular pump 518, the interior diameter of barrier plate 530 is first sealed to sleeve 144 with weld joint 122 and the outer diameter of barrier plate 530 is sealed to weld ring 146 with weld joint 523 to enclose electromagnetic coil 134 within recess 149. Then, in contrast to medical pump 200, a third weld joint, weld joint 524, attaches cover 570 to barrier plate 530 and weld ring 146. In this manner, the thickness of barrier plate 530 does not influence the height of protrusion 572 relative to magnetic cup 141 and weld ring 146.

Weld ring 146 forms notch 147, which is adjacent to an outer perimeter of cover 570. Likewise, base 579 of cover 570 forms notch 581, which is adjacent to notch 147 in weld ring 146. Weld joint 524 is partially located within notch 147, and weld joint 524 is also partially located within notch 581. In addition, base 579 also forms notch 583 at the inner diameter of base 579. Notch 583 is adjacent to the external diameter of barrier plate 530. Weld joint 523 is partially located within notch 583.

The combination of barrier plate 530, sleeve 144, weld ring 146 and weld joints 122, 523, 524 serve to fluidically separate an interior of magnetic cup 141 from an external surface of barrier plate 530, and thus separate the interior of magnetic cup 141 from fluid being pumped through magnetic pump 500. In addition, modular pump 518 is installed within bulkhead 280 such that weld ring 146 is sealed to cup-mounting bay 282 to fluidically separate an exterior of magnetic cup 141 from an external surface of barrier plate 530, and thus separate the exterior of magnetic cup 141 from fluid being pumped through magnetic pump 500. As examples, weld ring 146 may be interference fit within bulkhead 280 within cup-mounting bay 282 or sealed to bulkhead 280 with a weld joint or other suitable techniques. In this manner, the design of medical pump 500 completely separates magnetic cup 141 from fluid being pumped through magnetic pump 500.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of the disclosure have been described. However, modifications to the described examples may be made within the spirit of the disclosure. As an example, the described examples generally referred to medical pumps as delivering a therapeutic fluid to a target site within a patient. However, medical pumps may also be used to remove fluid from a patient. Specific examples of draining include using medical pumps to drain cerebrospinal fluid (CSF) from a patient and using medical pumps to drain other fluids from a cavity within a patient. These and other examples are within the scope of the following claims.

The invention claimed is:

1. A method comprising:
   individually measuring a volume of fluid delivered per pump stroke for each medical pump in a series of medical pumps manufactured according to the same design and specifications, wherein the medical pumps in the series each have a fixed stroke length;
   storing indications of the measured volumes for each medical pump in the series on one or more data storage mediums; and
   for each medical pump in the series, generating a separate therapy control program based on the indication of the measured volume associated with that one of the medical pumps in the series to calibrate the separate therapy control program to the measured volume associated with that one of the medical pumps in the series.

2. The method of claim 1, further comprising controlling each medical pump to deliver a specified quantity of therapeutic fluid based on the therapy control program associated with that medical pump.

3. The method of claim 2, wherein the specified quantity of therapeutic fluid is defined as a flow rate.

4. The method of claim 2, wherein the specified quantity of therapeutic fluid is defined as a volume of therapeutic fluid.

5. The method of claim 1, wherein the medical pumps are part of implantable medical devices (IMDs), and wherein storing indications of the measured volumes on one or more data storage mediums comprises storing each indication in a memory associated with the IMD corresponding to the medical pump associated with that indication.

6. The method of claim 5, wherein the memory is part of an external programmer that communicates wirelessly with the IMD to control delivery of a therapeutic fluid by the medical pump.

7. The method of claim 5, wherein the memory is part of the IMD.

8. The method of claim 1, wherein each medical pump in the series comprises:
 a magnetic cup forming a recess, wherein the magnetic cup includes a protrusion within the recess, wherein the cup forms a central aperture through the protrusion;
 a one-way valve that controls fluid flow within the central aperture;
 an electromagnetic coil within the recess and circumscribing the protrusion;
 a piston within the central aperture;
 a magnetic pole attached to the piston; and
 a cover enclosing the magnetic pole between an interior surface of the cover and the electromagnetic coil,
 wherein the cover includes one or more fixed protrusions on the interior surface of the cover, and wherein the protrusions set a stroke length of the piston.

9. The method of claim 8, wherein, for each medical pump in the series, the cover includes a filter within an inlet flow path of the medical pump.

10. The method of claim 8, wherein each medical pump in the series further comprises a barrier plate between the magnetic cup and the pole, wherein the barrier plate fluidically separates an interior of the cup from the external surface of the barrier plate.

11. The method of claim 10, wherein each medical pump in the series further comprises:
 a sleeve within the central aperture of the magnetic cup;
 a band fixed to the magnetic cup and surrounding the recess;
 a first seal between the sleeve and the barrier plate; and
 a first seal between the band and the barrier plate.

12. The method of claim 8, wherein each medical pump in the series further comprises a bulkhead that forms a cup-mounting bay, wherein the cup is mounted within the cup-mounting bay.

13. The method of claim 12, wherein, for each medical pump in the series, the bulkhead forms a filter-mounting bay and a fluid passageway that connects the filter-mounting bay to the cup-mounting bay, the medical pump assembly further comprising a filter mounted within the filter-mounting bay.

* * * * *